US012636333B1

(12) United States Patent (10) Patent No.: US 12,636,333 B1

Nguyen (45) Date of Patent: May 26, 2026

(54) HERBAL COMPOSITION FOR SUPPORTING RESTORATION OF DIGESTIVE SYSTEM FUNCTION AND METHOD FOR PRODUCING THE SAME

(71) Applicant: Thuy An Thi Nguyen, Ho Chi Minh (VN)

(72) Inventor: Thuy An Thi Nguyen, Ho Chi Minh (VN)

(73) Assignee: Thuy An Thi Nguyen, Ho Chi Minh (VN)

( * ) Notice: Subject to any disclaimer, the term of this patent is extended or adjusted under 35 U.S.C. 154(b) by 0 days.

(21) Appl. No.: 19/444,205

(22) Filed: Jan. 9, 2026

(51) Int. Cl.
| | |
|---|---|
| *A61K 36/00* | (2006.01) |
| *A61K 9/00* | (2006.01) |
| *A61K 36/185* | (2006.01) |
| *A61K 36/88* | (2006.01) |
| *A61K 47/26* | (2006.01) |
| *A61K 47/44* | (2017.01) |
| *A61K 47/46* | (2006.01) |

(52) U.S. Cl.
CPC .......... *A61K 36/185* (2013.01); *A61K 9/0053* (2013.01); *A61K 36/88* (2013.01); *A61K 47/26* (2013.01); *A61K 47/44* (2013.01); *A61K 47/46* (2013.01); *A61K 2236/13* (2013.01); *A61K 2236/15* (2013.01); *A61K 2236/17* (2013.01); *A61K 2236/333* (2013.01); *A61K 2236/51* (2013.01)

(58) Field of Classification Search
CPC ................................................. A61K 2236/333
See application file for complete search history.

*Primary Examiner* — Qiuwen Mi

(57) ABSTRACT

A herbal composition for supporting restoration of digestive system function comprising the following components: a *Leucaena leucocephala* extract, an eleutherin extract component from *Eleutherine bulbosa*, an *Andrographis paniculata* extract, a *Panax vietnamensis* extract, a *Pouzolzia zeylanica* extract, a first herbal mixture extract, a second herbal mixture extract, a sugar, a salt, a honey, a royal jelly, a vegetable oil, and a plant powder. Method for producing the composition comprising: (i) preparing materials; (ii) creating a base mixture; (iii) creating a first temporary mixture; (iv) creating a second temporary mixture; (v) creating a third temporary mixture; (vi) creating a fermented mixture; and (vii) packaging the fermented mixture to obtain the herbal composition for supporting restoration of digestive system function.

18 Claims, 1 Drawing Sheet

100

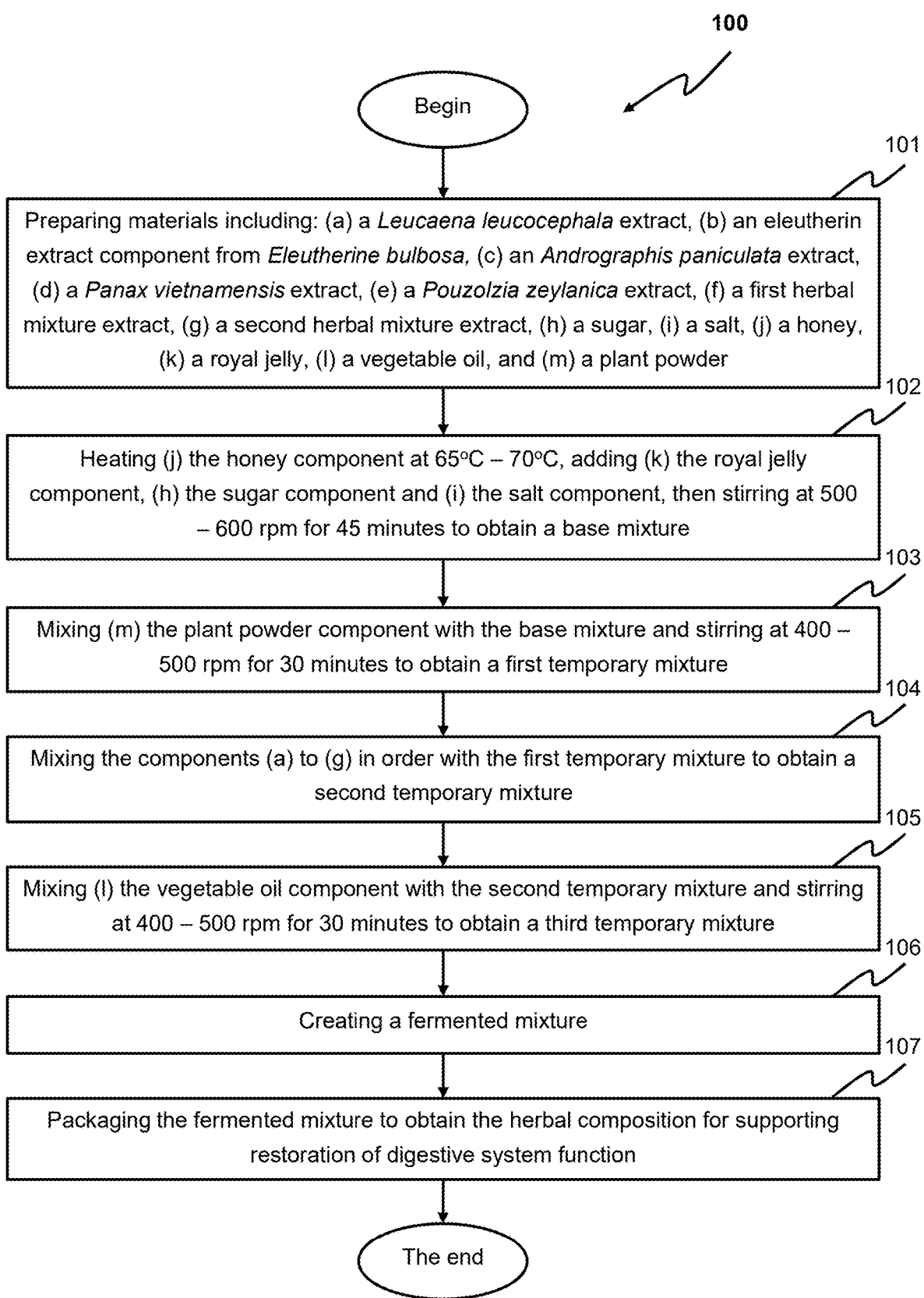

Begin

101

Preparing materials including: (a) a *Leucaena leucocephala* extract, (b) an eleutherin extract component from *Eleutherine bulbosa,* (c) an *Andrographis paniculata* extract, (d) a *Panax vietnamensis* extract, (e) a *Pouzolzia zeylanica* extract, (f) a first herbal mixture extract, (g) a second herbal mixture extract, (h) a sugar, (i) a salt, (j) a honey, (k) a royal jelly, (l) a vegetable oil, and (m) a plant powder

102

Heating (j) the honey component at 65°C – 70°C, adding (k) the royal jelly component, (h) the sugar component and (i) the salt component, then stirring at 500 – 600 rpm for 45 minutes to obtain a base mixture

103

Mixing (m) the plant powder component with the base mixture and stirring at 400 – 500 rpm for 30 minutes to obtain a first temporary mixture

104

Mixing the components (a) to (g) in order with the first temporary mixture to obtain a second temporary mixture

105

Mixing (l) the vegetable oil component with the second temporary mixture and stirring at 400 – 500 rpm for 30 minutes to obtain a third temporary mixture

106

Creating a fermented mixture

107

Packaging the fermented mixture to obtain the herbal composition for supporting restoration of digestive system function The end

HERBAL COMPOSITION FOR SUPPORTING RESTORATION OF DIGESTIVE SYSTEM FUNCTION AND METHOD FOR PRODUCING THE SAME

FIELD OF THE INVENTION

The present invention relates to health-protective compositions. More specifically, the invention concerns a herbal composition for supporting restoration of digestive system function and a method for producing the composition. The invention further relates to processes for extracting bioactive compounds from natural medicinal plants and to microbial fermentation, and to combining plant-derived components in predetermined proportions to provide a composition with high biological efficacy for balancing the gut microbiota and improving digestive function.

BACKGROUND ART

In the field of herbal drug technology and functional foods, numerous scientific reports and patents describe the use of herbal extracts or probiotic preparations to support digestive function and to balance the gut microbiota. Published methods typically focus on extracting one or a few common medicinal plants using conventional solvents, preparing single-strain or simple multi-strain probiotic formulations, or producing herbal products without combining a controlled, multi-strain fermentation process. Such documents rarely disclose an integrated process that combines specific extraction steps followed by a fermentation stage using a standardized probiotic consortium, together with pre-defined ratios of natural ingredients prior to fermentation.

In the area of functional food and herbal formulations for digestive support, many studies and technical solutions have been reported concerning the extraction of bioactive compounds from medicinal plants and the application of fermentative microorganisms. However, existing solutions often lack a comprehensive integration of raw material processing, optimized extraction, microbiological quality control, and fermentation conditions suitable for large-scale production. Some methods omit specific operating parameters, making reproduction and technology transfer difficult. In addition, blending multiple botanicals with different properties into a single, efficient process remains a significant technical challenge in practical manufacturing. Therefore, there remains a clear technical need for an integrated manufacturing method that is scalable to industrial production while ensuring stability, microbiological safety, and high yield of bioactive compounds.

Accordingly, it is desirable to provide a herbal composition for supporting restoration of digestive system function comprising the following components: a *Leucaena leucocephala* extract, an eleutherin extract component from *Eleutherine bulbosa*, an *Andrographis paniculata* extract, a *Panax vietnamensis* extract, a *Pouzolzia zeylanica* extract, a first herbal mixture extract, a second herbal mixture extract, a sugar, a salt, a honey, a royal jelly, a vegetable oil, and a plant powder.

It is further desirable to provide a method for producing a herbal composition for supporting restoration of digestive system function comprising: (i) preparing materials; (ii) creating a base mixture; (iii) creating a first temporary mixture; (iv) creating a second temporary mixture; (v) creating a third temporary mixture; (vi) creating a fermented mixture; and (vii) packaging the fermented mixture to obtain the herbal composition for supporting restoration of digestive system function.

Finally, it is desirable to provide a herbal composition that stabilizes and helps restore the intestinal microbiota, improves digestive capacity and nutrient absorption, and contributes to management of common gastrointestinal disorders. Additionally, the composition can help stabilize blood glucose, improve the condition of debilitated subjects, and is particularly useful for individuals at risk of reduced digestive function.

The present invention provides solutions to achieve these objectives.

SUMMARY OF THE INVENTION

Accordingly, a first aspect of the invention provides a method for producing a herbal composition for supporting restoration of digestive system function, comprising the following steps (i) to (vii):
  (i) preparing materials comprising:
    (a) a *Leucaena leucocephala* extract component having a predetermined first percentage (%) by weight, prepared by mixing a first extract, a second extract and a third extract at a weight ratio of 1:1:2;
    wherein the first extract is prepared by performing steps (a1) to (a4):
    (a1) preparing material: collecting *Leucaena leucocephala* roots, washing, cutting into pieces, drying to a moisture content of 10%-12%, grinding, and sieving through a 1-2 mm mesh to obtain a first powder;
    (a2) extracting the first powder with 60% ethanol at a ratio of 1:30 w/v at a temperature of 50° C.-60° C., in combination with ultrasonic treatment at a frequency of 30 kHz for 30 minutes to obtain a first temporary extract;
    (a3) filtering the first temporary extract to remove residues to obtain a filtered first temporary extract; and
    (a4) concentrating the filtered first temporary extract at a temperature of 65° C.-70° C. until a weight ratio of the first powder to the first extract reaches (1.5-2):1 to obtain the first extract;
    wherein the second extract is prepared by performing steps (a1') to (a4'):
    (a1') preparing material: collecting *Leucaena leucocephala* stems, washing, cutting into pieces, drying to a moisture content of 10%-12%, grinding, and sieving through a 1-2 mm mesh to obtain a second powder;
    (a2') extracting the second powder with 70% ethanol at a ratio of 1:30 w/v at a temperature of 50° C.-60° C., in combination with ultrasonic treatment at a frequency of 25 KHz for 25 minutes to obtain a second temporary extract;
    (a3') filtering the second temporary extract to remove residues to obtain a filtered second temporary extract; and
    (a4') concentrating the filtered second temporary extract at a temperature of 65° C.-70° C. until a ratio of the second powder to the second extract reaches (1.5-2):1 w/w to obtain the second extract;
    wherein the third extract is prepared by performing steps (a1") to (a4"):
    (a1") preparing material: collecting *Leucaena leucocephala* seeds, washing, drying to a moisture content of 10%-12%, grinding, and sieving through a 1-2 mm mesh to obtain a third powder;

(a2") extracting the third powder with 70% ethanol at a ratio of 1:30 w/v at a temperature of 50° C.-60° C., in combination with ultrasonic treatment at a frequency of 20 KHz for 20 minutes to obtain a third temporary extract;

(a3") filtering the third temporary extract to remove residues to obtain a filtered third temporary extract; and (a4") concentrating the filtered third temporary extract at a temperature of 65° C.-70° C. until a ratio of the third powder to the third extract reaches (1.5-2):1 w/w to obtain the third extract;

(b) an eleutherin extract component from *Eleutherine bulbosa* having a predetermined second percentage (%) by weight, prepared by performing steps (b1) to (b6):

(b1) preparing material: collecting *Eleutherine bulbosa* tubers, washing, drying to a moisture content of 10%-12%, grinding, and sieving through a 1-2 mm mesh to obtain an *Eleutherine bulbosa* powder;

(b2) extracting the *Eleutherine bulbosa* powder with 96% ethanol at a ratio of 1:25 w/v at a temperature of 50° C.-60° C., in combination with ultrasonic treatment at a frequency of 20 KHz for 20 minutes, and filtering to obtain an *Eleutherine bulbosa* temporary extract;

(b3) concentrating the *Eleutherine bulbosa* temporary extract by rotary evaporation at a temperature of 65° C.-70° C. to obtain an extract residue;

(b4) crystallizing the extract residue at 30° C.-35° C. for 48-72 hours, filtering and washing the crystals with 96% ethanol to obtain a crystalline residue;

(b5) treating the crystalline residue with 5% NaOH solution at 50° C.-60° C. for 10-15 minutes, then recrystallizing the material at 30° C.-35° C. and filtering the crystals from the NaOH solution to obtain alkali-treated crystals; and (b6) dissolving the alkali-treated crystals in 96% ethanol at 30° C.-35° C., cooling the solution to 5° C.-10° C. for 2-3 hours, filtering the crystals from ethanol and drying the crystals at 40° C.-50° C. for 90-120 minutes to obtain the eleutherin extract component;

(c) an *Andrographis paniculata* extract component having a predetermined third percentage (%) by weight, prepared by performing steps (c1) to (c4):

(c1) preparing material: collecting *Andrographis paniculata* leaves, washing, drying to a moisture content of 10%-12%, grinding, and sieving through a 1-2 mm mesh to obtain an *Andrographis paniculata* leaf powder;

(c2) extracting the *Andrographis paniculata* leaf powder with 70% ethanol at a ratio of 1:20 w/v at a temperature of 50° C.-60° C., in combination with ultrasonic treatment at a frequency of 25 kHz for 25 minutes, and filtering to remove residues to obtain an *Andrographis paniculata* extract;

(c3) concentrating the *Andrographis paniculata* extract by rotary evaporation at a temperature of 65° C.-70° C. to obtain an *Andrographis paniculata* extract residue; and (c4) mixing the *Andrographis paniculata* extract residue with water at a ratio of 1:1 w/w, then performing liquid-liquid extraction with ethyl acetate (EtOAc) in three repetitions, allowing phase separation and separating the ethyl acetate phase, combining the three ethyl acetate phases, and concentrating at a temperature of 50° C.-60° C. to remove the solvent, to obtain the *Andrographis paniculata* extract component;

(d) a *Panax vietnamensis* extract component having a predetermined fourth percentage (%) by weight, prepared by mixing a *Panax vietnamensis* root extract with a *Panax vietnamensis* stem and leaf extract at a ratio of 2:1 w/w;

wherein the *Panax vietnamensis* root extract is prepared by performing steps (d1) to (d4):

(d1) preparing material: collecting *Panax vietnamensis* roots of 3-5 years old, washing, cutting into pieces, drying to a moisture content of 10%-12%, grinding, and sieving through a 1-2 mm mesh to obtain a *Panax vietnamensis* root powder;

(d2) mixing the *Panax vietnamensis* root powder with water at a ratio of 1:10 w/w, adding cellulase to achieve an activity of 280-300 U/g in the mixture and adding pectinase to achieve an activity of 220-250 U/g in the mixture, then incubating at a temperature of 45° C.-50° C. with agitation at 120-150 rpm for 1.5-2 hours, followed by ultrasonic-assisted extraction at a frequency of 25 kHz with agitation at 80-100 rpm at 60° C.-65° C. for 25-30 minutes, and centrifuging at 800 rpm for 20 minutes to obtain a solid residue from the root material and a first *Panax vietnamensis* root extract;

(d3) extracting the solid residue from the root material with 60% ethanol at a ratio of 1:20 w/v at a temperature of 50° C.-60° C., in combination with ultrasonic treatment at a frequency of 30 KHz for 30 minutes, and filtering to obtain a second *Panax vietnamensis* root extract; and (d4) combining the first *Panax vietnamensis* root extract and the second *Panax vietnamensis* root extract, concentrating the combined root extract at a temperature of 65° C.-70° C. until a ratio of the *Panax vietnamensis* root powder to the combined root extract reaches (1.5-2):1 w/w to obtain the *Panax vietnamensis* root extract;

wherein the *Panax vietnamensis* stem and leaf extract is prepared by performing steps (d1') to (d4'):

(d1') preparing material: collecting *Panax vietnamensis* stems and leaves, washing, cutting into pieces, drying to a moisture content of 10%-12%, grinding, and sieving through a 1-2 mm mesh to obtain a *Panax vietnamensis* stem and leaf powder;

(d2') mixing the *Panax vietnamensis* stem and leaf powder with water at a ratio of 1:10 w/w, adding cellulase to achieve an activity of 220-250 U/g in the mixture, then incubating at a temperature of 45° C.-50° C. with agitation at 100-120 rpm for 1.5-2 hours, followed by ultrasonic-assisted extraction at a frequency of 20 kHz with agitation at 80-100 rpm at 60° C.-65° C. for 20-25 minutes, and centrifuging at 800 rpm for 20 minutes to obtain a solid residue from the stem and leaf material and a first *Panax vietnamensis* stem and leaf extract;

(d3') extracting the solid residue from the stem and leaf material with 70% ethanol at a ratio of 1:20 w/v at a temperature of 50° C.-60° C., in combination with ultrasonic treatment at a frequency of 20 KHz for 20 minutes, and filtering to obtain a second *Panax vietnamensis* stem and leaf extract; and (d4') combining the first *Panax vietnamensis* stem and leaf extract and the second *Panax vietnamensis* stem and leaf extract, concentrating the combined stem and leaf extract at a temperature of 65° C.-70° C. until a ratio of the *Panax vietnamensis* stem and leaf powder to the combined stem and leaf extract reaches (1.5-2):1 w/w to obtain the *Panax vietnamensis* stem and leaf extract;

(e) a *Pouzolzia zeylanica* extract component having a predetermined fifth percentage (%) by weight, prepared by performing steps (e1) to (e4):

(e1) preparing material: collecting *Pouzolzia zeylanica* stems and leaves, washing, cutting into pieces, drying to a moisture content of 10%-12%, grinding, and sieving through a 1-2 mm mesh to obtain a *Pouzolzia zeylanica* powder;

(e2) mixing the *Pouzolzia zeylanica* powder with water at a weight ratio of 1:10 w/w, adding cellulase to achieve an activity of 280-300 U/g in the mixture, then incubating at a temperature of 45° C.-50° C. with agitation at 100-120 rpm for 1.5-2 hours, followed by ultrasonic-assisted extraction at a frequency of 25 kHz with agitation at 80-100 rpm at 60° C.-65° C. for 20-25 minutes, and centrifuging at 800 rpm for 20 minutes to obtain a solid residue from the material and a first *Pouzolzia zeylanica* extract;

(e3) extracting the solid residue from the material with 70% ethanol at a ratio of 1:20 w/v at a temperature of 50° C.-60° C., in combination with ultrasonic treatment at a frequency of 25 kHz for 30 minutes, and filtering to obtain a second *Pouzolzia zeylanica* extract; and (e4) combining the first *Pouzolzia zeylanica* extract and the second *Pouzolzia zeylanica* extract, concentrating the combined extract at a temperature of 65° C.-70° C. until a ratio of the *Pouzolzia zeylanica* powder to the combined extract reaches (1.5-2):1 w/w to obtain the *Pouzolzia zeylanica* extract component;

(f) a first herbal mixture extract component having a predetermined sixth percentage (%) by weight, prepared by performing steps (f1) to (f4):

(f1) preparing a first herbal mixture powder by mixing five herbals at a weight ratio of 2 parts of *Curcuma zedoaria* root, 2 parts of *Curcuma longa* root, 2 parts of *Zingiber officinale* root, 2 parts of *Alpinia galanga* root, 1 part of *Platycodon grandiflorus* root and 1 part of *Citrus aurantium* fruit, each herbal having a moisture content of 10%-12%, and grinding and sieving the blended materials through a 1-2 mm mesh to obtain a first herbal mixture powder;

(f2) mixing the first herbal mixture powder with water at a ratio of 1:(15-20) w/w, adding cellulase to achieve an activity of 650-700 U/g in the mixture and adding pectinase to achieve an activity of 450-500 U/g in the mixture, then incubating at a temperature of 40° C.-45° C. with agitation at 100-150 rpm for 2-3 hours, followed by ultrasonic-assisted extraction at a frequency of 30 kHz with agitation at 80-100 rpm at 65° C.-70° C. for 30 minutes, and centrifuging at 800 rpm for 20 minutes to obtain a solid residue from the first herbal mixture and a first extract of the first herbal mixture;

(f3) extracting the solid residue from the first herbal mixture with 70% ethanol at a ratio of 1:(10-15) w/v at a temperature of 55° C.-60° C., in combination with ultrasonic treatment at a frequency of 25 kHz with agitation at 80-100 rpm for 20 minutes, followed by centrifuging at 800 rpm for 20 minutes and filtering to obtain a second extract of the first herbal mixture; and (f4) combining the first extract of the first herbal mixture and the second extract of the first herbal mixture, concentrating the combined first herbal mixture extract at a temperature of 65° C.-70° C. until a ratio of the first herbal mixture powder to the combined first herbal mixture extract reaches (1.5-2):1 w/w to obtain the first herbal mixture extract component;

(g) a second herbal mixture extract component having a predetermined seventh percentage (%) by weight, prepared by performing steps (g1) to (g4):

(g1) preparing a second herbal mixture by mixing five herbals at a weight ratio of 3 parts of *Plumbago zeylanica* stem, 3 parts of *Cleistocalyx operculatus* leaf, 2 parts of *Ampelopsis cantoniensis* leaf, 1 part of whole plant of *Lycopodiella cernua*, and 1 part of *Ficus carica* fruit, each herbal material having a moisture content of 10%-12%, and grinding and sieving the blended materials through a 1-2 mm mesh to obtain a second herbal mixture powder;

(g2) mixing the second herbal mixture powder with water at a weight ratio of 1:(20-25) w/w, adding cellulase to achieve an activity of 550-600 U/g in the mixture and adding pectinase to achieve an activity of 350-400 U/g in the mixture, incubating at a temperature of 40° C.-45° C. with agitation at 100-150 rpm for 2-3 hours, followed by ultrasonic-assisted extraction at a frequency of 30 KHz with agitation at 80-100 rpm at 65° C.-70° C. for 30 minutes, and centrifuging at 800 rpm for 20 minutes to obtain a solid residue from the second herbal mixture and a first extract of the second herbal mixture;

(g3) extracting the solid residue from the second herbal mixture with 70% ethanol at a ratio of 1:(10-15) w/v at a temperature of 55° C.-60° C., in combination with ultrasonic treatment at a frequency of 20 kHz with agitation at 80-100 rpm for 20 minutes, followed by centrifuging at 800 rpm for 20 minutes and removing the solid residue to obtain a second extract of the second herbal mixture; and (g4) combining the first extract of the second herbal mixture and the second extract of the second herbal mixture, concentrating the combined second herbal mixture extract at a temperature of 65° C.-70° C. until a ratio of the second herbal mixture powder to the combined second herbal mixture extract reaches (1.5-2):1 w/w to obtain the second herbal mixture extract component;

(h) a sugar component having a predetermined eighth percentage (%) by weight;

wherein the sugar component is selected from the group consisting of glucose, fructose, galactose, lactose, maltose, sucrose, and combinations thereof;

(i) a salt component having a predetermined ninth percentage (%) by weight;

wherein the salt component is selected from the group consisting of sea salt, himalayan pink salt, kosher salt, and combinations thereof;

(j) a honey component having a predetermined tenth percentage (%) by weight;

(k) a royal jelly component having a predetermined eleventh percentage (%) by weight;

(l) a vegetable oil component having a predetermined twelfth percentage (%) by weight;

wherein the vegetable oil component is selected from the group consisting of rice bran oil, sunflower oil, olive oil, and combinations thereof; and (m) a plant powder component having a predetermined thirteenth percentage (%) by weight;

wherein the plant powder component is selected from the group consisting of rice flour, wheat flour, cereal flour, and combinations thereof;

wherein the cereal flour is obtained by mixing five legume seed powders at a weight ratio of 1 part of *Vigna unguiculata* seed powder, 1 part of *Glycine max* seed powder, 1 part of *Vigna radiata* seed powder, 1 part of *Vigna angularis* seed powder, and 1 part of *Phaseolus vulgaris* seed powder;

(ii) heating the honey component at 65° C.-70° C., adding the royal jelly component, the sugar component and the salt component, then stirring at 500-600 rpm for 45 minutes to obtain a base mixture;

(iii) mixing the plant powder component with the base mixture at step (ii) and stirring at 400-500 rpm for 30 minutes to obtain a first temporary mixture;

(iv) mixing the components (a) to (g) in order with the first temporary mixture at step (iii) to obtain a second temporary mixture, ensuring homogeneous mixing after each addition; and (v) mixing the vegetable oil component with the second temporary mixture at step (iv) and stirring at 400-500 rpm for 30 minutes to obtain a third temporary mixture;

(vi) creating a fermented mixture by performing steps (i') to (iii'):

(i') preparing ingredients comprising a substrate mixture and a fermentation microbial mixture;

wherein the substrate mixture is obtained by sterilizing the third temporary mixture at step (v) by autoclaving at 121° C. for 15 minutes;

wherein the fermentation microbial mixture is obtained by mixing a first microbial biomass, a second microbial biomass, a third microbial biomass and a fourth microbial biomass at a weight ratio of 1:1:1:1; wherein the first microbial biomass is obtained by culturing *Lactobacillus plantarum* (ATCC 14917) on a propagation medium for 24 hours at 37° C., then centrifuging at 4° C. at 6000 rpm for 10 minutes, removing the supernatant and collecting the microbial pellet to obtain the first microbial biomass;

the second microbial biomass is obtained by culturing *Lactobacillus fermentum* (ATCC 23271) on a propagation medium for 24 hours at 37° C., then centrifuging at 4° C. at 6000 rpm for 10 minutes, removing the supernatant and collecting the microbial pellet to obtain the second microbial biomass;

the third microbial biomass is obtained by culturing *Lactobacillus rhamnosus* (ATCC 53103) on a propagation medium for 24 hours at 37° C., then centrifuging at 4° C. at 6000 rpm for 10 minutes, removing the supernatant and collecting the microbial pellet to obtain the third microbial biomass; and the fourth microbial biomass is obtained by culturing *Lactobacillus paracasei* (ATCC 25598) on a propagation medium for 24 hours at 37° C., then centrifuging at 4° C. at 6000 rpm for 10 minutes, removing the supernatant and collecting the microbial pellet to obtain the fourth microbial biomass;

wherein the propagation medium comprises glucose 20 g/L, peptone 10 g/L, yeast extract 5 g/L, $CaCO_3$ 5 g/L, $K_2HPO_4$ 2 g/L, $MgSO_4$ 0.6 g/L, and $MnSO_4$ 0.3 g/L;

(ii') mixing the fermentation microbial mixture with the substrate mixture at a ratio of (1-2):100 w/w, and mixing until homogeneous to obtain a fermentation substrate mixture; and (iii') fermenting the fermentation substrate mixture at 30° C.-35° C. for 40-48 hours to obtain the fermented mixture;

wherein the total viable cell density in the fermented mixture is $1 \times 10^7$ to $1 \times 10^9$ CFU/g; and (vii) packaging the fermented mixture at step (vi) to obtain the herbal composition for supporting restoration of digestive system function.

A second aspect of the invention provides a herbal composition for supporting restoration of digestive system function comprising: (a) a *Leucaena leucocephala* extract component having a predetermined first percentage (%) by weight, (b) an eleutherin extract component from *Eleutherine bulbosa* having a predetermined second percentage (%) by weight, (c) an *Andrographis paniculata* extract component having a predetermined third percentage (%) by weight, (d) a *Panax vietnamensis* extract component having a predetermined fourth percentage (%) by weight, (e) a *Pouzolzia zeylanica* extract component having a predetermined fifth percentage (%) by weight, (f) a first herbal mixture extract component having a predetermined sixth percentage (%) by weight, (g) a second herbal mixture extract component having a predetermined seventh percentage (%) by weight, (h) a sugar component having a predetermined eighth percentage (%) by weight, (i) a salt component having a predetermined ninth percentage (%) by weight, (j) a honey component having a predetermined tenth percentage (%) by weight, (k) a royal jelly component having a predetermined eleventh percentage (%) by weight, (l) a vegetable oil component having a predetermined twelfth percentage (%) by weight, and (m) a plant powder component having a predetermined thirteenth percentage (%) by weight.

A third aspect of the invention provides a herbal composition for supporting restoration of digestive system function comprising: the predetermined first percentage (%) by weight is 6%-8%, the predetermined second percentage (%) by weight is 4%-6%, the predetermined third percentage (%) by weight is 3%-5%, the predetermined fourth percentage (%) by weight is 6%-8%, the predetermined fifth percentage (%) by weight is 4%-6%, the predetermined sixth percentage (%) by weight is 18%-20%, the predetermined seventh percentage (%) by weight is 12%-14%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

A fourth aspect of the invention provides a herbal composition for supporting restoration of digestive system function comprising: the predetermined first percentage (%) by weight is 4%-6%, the predetermined second percentage (%) by weight is 4%-6%, the predetermined third percentage (%) by weight is 8%-10%, the predetermined fourth percentage (%) by weight is 6%-8%, the predetermined fifth percentage (%) by weight is 2%-4%, the predetermined sixth percentage (%) by weight is 18%-20%, the predetermined seventh percentage (%) by weight is 10%-12%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

A fifth aspect of the invention provides a herbal composition for supporting restoration of digestive system function comprising: the predetermined first percentage (%) by weight is 6%-8%, the predetermined second percentage (%) by weight is 4%-5%, the predetermined third percentage (%) by weight is 3%-4%, the predetermined fourth percentage (%) by weight is 6%-8%, the predetermined fifth percentage (%) by weight is 6%-8%, the predetermined sixth percentage (%) by weight is 6%-8%, the predetermined seventh percentage (%) by weight is 12%-14%, the predetermined eighth percentage (%) by weight is 3%-4%, the predetermined ninth percentage (%) by weight is 0.5%-1.5%, the predetermined tenth percentage (%) by weight is 10%-12%, the predetermined eleventh percentage (%) by weight is 10%-12%, the predetermined twelfth percentage (%) by weight is 2%-3%, and the thirteenth percentage (%) by weight is the remainder to make up 100% by weight.

Finally, a sixth aspect of the invention provides a herbal composition for supporting restoration of digestive system function comprising: the predetermined first percentage (%) by weight is 4%-6%, the predetermined second percentage (%) by weight is 5%-6%, the predetermined third percentage (%) by weight is 5%-7%, the predetermined fourth percentage (%) by weight is 14%-16%, the predetermined fifth percentage (%) by weight is 4%-6%, the predetermined sixth percentage (%) by weight is 16%-18%, the predetermined seventh percentage (%) by weight is 8%-10%, the predetermined eighth percentage (%) by weight is 2%-3%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

FIG. 1 is a flowchart illustrating a method for producing a herbal composition for supporting restoration of digestive system function.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

It should be noted that the terms "comprises" and "comprising", as well as "the" and "these", are intended to cover a non-exclusive inclusion. For example, a process, method, system, product, or device that comprises a series of steps or units is not necessarily limited to those explicitly listed and may include other steps or units not explicitly mentioned or inherent to such processes, methods, products, or devices.

In the embodiment of the present invention, percent mass or percentage (%) by weight=(mass of solute/mass of solution)×100%. The unit of mass is usually grams, or kilograms. Mass percent is also known as the correct percentage by weight or w/w %. It should also be noted that the molar mass is also within the meaning of the invention. Molar mass is the total mass of all atoms in a mole of compound. Total all volume percentages add up to 100%.

It should also be noted that the term "homogeneous" or "mixing homogenizing" is used in the invention understood to mean the uniform distribution, or complete dissolution of, substances present in a solution/mixture.

It should be noted that the terms "admixed/mixed/admixing/mixing" as used in the present invention is understood to mean adding, or reacting, or dissolving homogeneously, or evenly, components in the same solution/mixture.

As the plant extracted or herbal extracted or medicine herbal extracted in the present invention, an "extracts" extracted as an active compound contained in any of the plants mentioned. The plant extract in an active compounds sense obtained by steam distillation from the above plants or dried materials thereof is preferably used as the "extracts" in the present invention, but is not limited thereto. For example, active compounds extracted from the plants by using other methods such as extraction or expression are also included in the "extracts" of the present invention as long as they contain extracted components (such as active compounds). Other methods for extracting active compounds from plants, for example, solvent extraction (such as alcohol extraction, organic solvent extraction), oil and fat adsorption extraction (hot effleurage or cold effleurage), and supercritical fluid extraction are known. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts" in the present invention may be those in which the active compounds obtained by the above method is further purified and concentrated by using various purification procedures such as hydrophobic or adsorptive chromatography using a support such as porous beads, silica gel, or alumina.

One embodiment of the invention is now described with reference to FIG. 1. FIG. 1 illustrates a flowchart illustrating a method for producing a herbal composition for supporting restoration of digestive system function 100 ("method 100") based on the above principle in accordance with an exemplary embodiment of the present invention. In particular, method 100 includes the following steps:

At step 101, preparing materials comprising: (a) a *Leucaena leucocephala* extract component having a predetermined first percentage (%) by weight, (b) an eleutherin extract component from *Eleutherine bulbosa* having a predetermined second percentage (%) by weight, (c) an *Andrographis paniculata* extract component having a predetermined third percentage (%) by weight, (d) a *Panax vietnamensis* extract component having a predetermined fourth percentage (%) by weight, (e) a *Pouzolzia zeylanica* extract component having a predetermined fifth percentage (%) by weight, (f) a first herbal mixture extract component having a predetermined sixth percentage (%) by weight, (g) a second herbal mixture extract component having a predetermined seventh percentage (%) by weight, (h) a sugar component having a predetermined eighth percentage (%) by weight, (i) a salt component having a predetermined ninth percentage (%) by weight, (j) a honey component having a predetermined tenth percentage (%) by weight, (k) a royal jelly component having a predetermined eleventh percentage (%) by weight, (I) a vegetable oil component having a predetermined twelfth percentage (%) by weight, and (m) a plant powder component having a predetermined thirteenth percentage (%) by weight.

In the present invention, (a) a *Leucaena leucocephala* extract component having a predetermined first percentage (%) by weight, prepared by mixing a first extract, a second extract and a third extract at a weight ratio of 1:1:2.

The first extract is prepared by performing steps (a1) to (a4):

(a1) preparing material: collecting *Leucaena leucocephala* roots, washing, cutting into pieces, drying to a moisture content of 10%-12%, grinding, and sieving through a 1-2 mm mesh to obtain a first powder;

(a2) extracting the first powder with 60% ethanol at a ratio of 1:30 w/v at a temperature of 50° C.-60° C., in combination with ultrasonic treatment at a frequency of 30 kHz for 30 minutes to obtain a first temporary extract;

(a3) filtering the first temporary extract to remove residues to obtain a filtered first temporary extract; and (a4) concentrating the filtered first temporary extract at a temperature of 65° C.-70° C. until a weight ratio of the first powder to the first extract reaches (1.5-2):1 to obtain the first extract.

The second extract is prepared by performing steps (a1') to (a4'):

(a1') preparing material: collecting *Leucaena leucocephala* stems, washing, cutting into pieces, drying to a moisture content of 10%-12%, grinding, and sieving through a 1-2 mm mesh to obtain a second powder;

(a2') extracting the second powder with 70% ethanol at a ratio of 1:30 w/v at a temperature of 50° C.-60° C., in combination with ultrasonic treatment at a frequency of 25 kHz for 25 minutes to obtain a second temporary extract;

(a3') filtering the second temporary extract to remove residues to obtain a filtered second temporary extract; and (a4') concentrating the filtered second temporary extract at a temperature of 65° C.-70° C. until a ratio of the second powder to the second extract reaches (1.5-2):1 w/w to obtain the second extract.

The third extract is prepared by performing steps (a1") to (a4"):

(a1") preparing material: collecting *Leucaena leucocephala* seeds, washing, drying to a moisture content of 10%-12%, grinding, and sieving through a 1-2 mm mesh to obtain a third powder;

(a2") extracting the third powder with 70% ethanol at a ratio of 1:30 w/v at a temperature of 50° C.-60° C., in combination with ultrasonic treatment at a frequency of 20 KHz for 20 minutes to obtain a third temporary extract;

(a3") filtering the third temporary extract to remove residues to obtain a filtered third temporary extract; and (a4") concentrating the filtered third temporary extract at a temperature of 65° C.-70° C. until a ratio of the third powder to the third extract reaches (1.5-2):1 w/w to obtain the third extract.

In the present invention, (b) an eleutherin extract component from *Eleutherine bulbosa* having a predetermined second percentage (%) by weight, prepared by performing steps (b1) to (b6):

(b1) preparing material: collecting *Eleutherine bulbosa* tubers, washing, drying to a moisture content of 10%-12%, grinding, and sieving through a 1-2 mm mesh to obtain an *Eleutherine bulbosa* powder;

(b2) extracting the *Eleutherine bulbosa* powder with 96% ethanol at a ratio of 1:25 w/v at a temperature of 50° C.-60° C., in combination with ultrasonic treatment at a frequency of 20 KHz for 20 minutes, and filtering to obtain an *Eleutherine bulbosa* temporary extract;

(b3) concentrating the *Eleutherine bulbosa* temporary extract by rotary evaporation at a temperature of 65° C.-70° C. to obtain an extract residue;

(b4) crystallizing the extract residue at 30° C.-35° C. for 48-72 hours, filtering and washing the crystals with 96% ethanol to obtain a crystalline residue;

(b5) treating the crystalline residue with 5% NaOH solution at 50° C.-60° C. for 10-15 minutes, then recrystallizing the material at 30° C.-35° C. and filtering the crystals from the NaOH solution to obtain alkali-treated crystals; and (b6) dissolving the alkali-treated crystals in 96% ethanol at 30° C.-35° C., cooling the solution to 5° C.-10° C. for 2-3 hours, filtering the crystals from ethanol and drying the crystals at 40° C.-50° C. for 90-120 minutes to obtain the eleutherin extract component.

In the present invention, (c) an *Andrographis paniculata* extract component having a predetermined third percentage (%) by weight, prepared by performing steps (c1) to (c4):

(c1) preparing material: collecting *Andrographis paniculata* leaves, washing, drying to a moisture content of 10%-12%, grinding, and sieving through a 1-2 mm mesh to obtain an *Andrographis paniculata* leaf powder;

(c2) extracting the *Andrographis paniculata* leaf powder with 70% ethanol at a ratio of 1:20 w/v at a temperature of 50° C.-60° C., in combination with ultrasonic treatment at a frequency of 25 kHz for 25 minutes, and filtering to remove residues to obtain an *Andrographis paniculata* extract;

(c3) concentrating the *Andrographis paniculata* extract by rotary evaporation at a temperature of 65° C.-70° C. to obtain an *Andrographis paniculata* extract residue; and (c4) mixing the *Andrographis paniculata* extract residue with water at a ratio of 1:1 w/w, then performing liquid-liquid extraction with ethyl acetate (EtOAc) in three repetitions, allowing phase separation and separating the ethyl acetate phase, combining the three ethyl acetate phases, and concentrating at a temperature of 50° C.-60° C. to remove the solvent, to obtain the *Andrographis paniculata* extract component.

In the present invention, (d) a *Panax vietnamensis* extract component having a predetermined fourth percentage (%) by weight, prepared by mixing a *Panax vietnamensis* root extract with a *Panax vietnamensis* stem and leaf extract at a ratio of 2:1 w/w.

The *Panax vietnamensis* root extract is prepared by performing steps (d1) to (d4):

(d1) preparing material: collecting *Panax vietnamensis* roots of 3-5 years old, washing, cutting into pieces, drying to a moisture content of 10%-12%, grinding, and sieving through a 1-2 mm mesh to obtain a *Panax vietnamensis* root powder;

(d2) mixing the *Panax vietnamensis* root powder with water at a ratio of 1:10 w/w, adding cellulase to achieve an activity of 280-300 U/g in the mixture and adding pectinase to achieve an activity of 220-250 U/g in the mixture, then incubating at a temperature of 45° C.-50° C. with agitation at 120-150 rpm for 1.5-2 hours, followed by ultrasonic-assisted extraction at a frequency of 25 kHz with agitation at 80-100 rpm at 60° C.-65° C. for 25-30 minutes, and centrifuging at 800 rpm for 20 minutes to obtain a solid residue from the root material and a first *Panax vietnamensis* root extract;

(d3) extracting the solid residue from the root material with 60% ethanol at a ratio of 1:20 w/v at a temperature of 50° C.-60° C., in combination with ultrasonic treatment at a frequency of 30 kHz for 30 minutes, and filtering to obtain a second *Panax vietnamensis* root extract; and (d4) combining the first *Panax vietnamensis* root extract and the second *Panax vietnamensis* root extract, concentrating the combined root extract at a temperature of 65° C.-70° C. until a ratio of the *Panax vietnamensis* root powder to the combined root extract reaches (1.5-2):1 w/w to obtain the *Panax vietnamensis* root extract.

The *Panax vietnamensis* stem and leaf extract is prepared by performing steps (d1') to (d4'):

(d1') preparing material: collecting *Panax vietnamensis* stems and leaves, washing, cutting into pieces, drying to a moisture content of 10%-12%, grinding, and sieving through a 1-2 mm mesh to obtain a *Panax vietnamensis* stem and leaf powder;

(d2') mixing the *Panax vietnamensis* stem and leaf powder with water at a ratio of 1:10 w/w, adding cellulase to achieve an activity of 220-250 U/g in the mixture, then incubating at a temperature of 45° C.-50° C. with agitation at 100-120 rpm for 1.5-2 hours, followed by ultrasonic-assisted extraction at a frequency of 20 KHz with agitation at 80-100 rpm at 60° C.-65° C. for 20-25 minutes, and centrifuging at 800 rpm for 20 minutes to obtain a solid residue from the stem and leaf material and a first *Panax vietnamensis* stem and leaf extract;

(d3') extracting the solid residue from the stem and leaf material with 70% ethanol at a ratio of 1:20 w/v at a temperature of 50° C.-60° C., in combination with ultrasonic treatment at a frequency of 20 KHz for 20 minutes, and filtering to obtain a second *Panax vietnamensis* stem and leaf extract; and (d4') combining the first *Panax vietnamensis* stem and leaf extract and the second *Panax vietnamensis* stem and leaf extract, concentrating the combined stem and leaf extract at a temperature of 65° C.-70° C. until a ratio of the *Panax vietnamensis* stem and leaf powder to the combined stem and leaf extract reaches (1.5-2):1 w/w to obtain the *Panax vietnamensis* stem and leaf extract.

In the present invention, (e) a *Pouzolzia zeylanica* extract component having a predetermined fifth percentage (%) by weight, prepared by performing steps (e1) to (e4):

(e1) preparing material: collecting *Pouzolzia zeylanica* stems and leaves, washing, cutting into pieces, drying to a moisture content of 10%-12%, grinding, and sieving through a 1-2 mm mesh to obtain a *Pouzolzia zeylanica* powder;

(e2) mixing the *Pouzolzia zeylanica* powder with water at a weight ratio of 1:10 w/w, adding cellulase to achieve an activity of 280-300 U/g in the mixture, then incubating at a temperature of 45° C.-50° C. with agitation at 100-120 rpm for 1.5-2 hours, followed by ultrasonic-assisted extraction at a frequency of 25 kHz with agitation at 80-100 rpm at 60° C.-65° C. for 20-25 minutes, and centrifuging at 800 rpm for 20 minutes to obtain a solid residue from the material and a first *Pouzolzia zeylanica* extract;

(e3) extracting the solid residue from the material with 70% ethanol at a ratio of 1:20 w/v at a temperature of 50° C.-60° C., in combination with ultrasonic treatment at a frequency of 25 KHz for 30 minutes, and filtering to obtain a second *Pouzolzia zeylanica* extract; and (e4) combining the first *Pouzolzia zeylanica* extract and the second *Pouzolzia zeylanica* extract, concentrating the combined extract at a temperature of 65° C.-70° C. until a ratio of the *Pouzolzia zeylanica* powder to the combined extract reaches (1.5-2):1 w/w to obtain the *Pouzolzia zeylanica* extract component.

In the present invention, (f) a first herbal mixture extract component having a predetermined sixth percentage (%) by weight, prepared by performing steps (f1) to (f4):

(f1) preparing a first herbal mixture powder by mixing five herbals at a weight ratio of 2 parts of *Curcuma zedoaria* root, 2 parts of *Curcuma longa* root, 2 parts of *Zingiber officinale* root, 2 parts of *Alpinia galanga* root, 1 part of *Platycodon grandiflorus* root and 1 part of *Citrus aurantium* fruit, each herbal having a moisture content of 10%-12%, and grinding and sieving the blended materials through a 1-2 mm mesh to obtain a first herbal mixture powder;

(f2) mixing the first herbal mixture powder with water at a ratio of 1:(15-20) w/w, adding cellulase to achieve an activity of 650-700 U/g in the mixture and adding pectinase to achieve an activity of 450-500 U/g in the mixture, then incubating at a temperature of 40° C.-45° C. with agitation at 100-150 rpm for 2-3 hours, followed by ultrasonic-assisted extraction at a frequency of 30 KHz with agitation at 80-100 rpm at 65° C.-70°

15

C. for 30 minutes, and centrifuging at 800 rpm for 20 minutes to obtain a solid residue from the first herbal mixture and a first extract of the first herbal mixture;

(f3) extracting the solid residue from the first herbal mixture with 70% ethanol at a ratio of 1:(10-15) w/v at a temperature of 55° C.-60° C., in combination with ultrasonic treatment at a frequency of 25 kHz with agitation at 80-100 rpm for 20 minutes, followed by centrifuging at 800 rpm for 20 minutes and filtering to obtain a second extract of the first herbal mixture; and (f4) combining the first extract of the first herbal mixture and the second extract of the first herbal mixture, concentrating the combined first herbal mixture extract at a temperature of 65° C.-70° C. until a ratio of the first herbal mixture powder to the combined first herbal mixture extract reaches (1.5-2):1 w/w to obtain the first herbal mixture extract component.

In the present invention, (g) a second herbal mixture extract component having a predetermined seventh percentage (%) by weight, prepared by performing steps (g1) to (g4):

(g1) preparing a second herbal mixture by mixing five herbals at a weight ratio of 3 parts of *Plumbago zeylanica* stem, 3 parts of *Cleistocalyx operculatus* leaf, 2 parts of *Ampelopsis cantoniensis* leaf, 1 part of whole plant of *Lycopodiella cernua*, and 1 part of *Ficus carica* fruit, each herbal material having a moisture content of 10%-12%, and grinding and sieving the blended materials through a 1-2 mm mesh to obtain a second herbal mixture powder;

(g2) mixing the second herbal mixture powder with water at a weight ratio of 1:(20-25) w/w, adding cellulase to achieve an activity of 550-600 U/g in the mixture and adding pectinase to achieve an activity of 350-400 U/g in the mixture, incubating at a temperature of 40° C.-45° C. with agitation at 100-150 rpm for 2-3 hours, followed by ultrasonic-assisted extraction at a frequency of 30 kHz with agitation at 80-100 rpm at 65° C.-70° C. for 30 minutes, and centrifuging at 800 rpm for 20 minutes to obtain a solid residue from the second herbal mixture and a first extract of the second herbal mixture;

(g3) extracting the solid residue from the second herbal mixture with 70% ethanol at a ratio of 1:(10-15) w/v at a temperature of 55° C.-60° C., in combination with ultrasonic treatment at a frequency of 20 KHz with agitation at 80-100 rpm for 20 minutes, followed by centrifuging at 800 rpm for 20 minutes and removing the solid residue to obtain a second extract of the second herbal mixture; and (g4) combining the first extract of the second herbal mixture and the second extract of the second herbal mixture, concentrating the combined second herbal mixture extract at a temperature of 65° C.-70° C. until a ratio of the second herbal mixture powder to the combined second herbal mixture extract reaches (1.5-2):1 w/w to obtain the second herbal mixture extract component.

In the present invention, (h) a sugar component having a predetermined eighth percentage (%) by weight;

wherein the sugar component is selected from the group consisting of glucose, fructose, galactose, lactose, maltose, sucrose, and combinations thereof.

According to the preferred embodiment of the present invention, the sugar component is sucrose.

In the present invention, (i) a salt component having a predetermined ninth percentage (%) by weight;

wherein the salt component is selected from the group consisting of sea salt, himalayan pink salt, kosher salt, and combinations thereof.

According to the preferred embodiment of the present invention, the salt component is obtained by mixing sea salt and himalayan pink salt at a weight ratio of 1:1.

In the present invention, (j) a honey component having a predetermined tenth percentage (%) by weight.

In the present invention, (k) a royal jelly component having a predetermined eleventh percentage (%) by weight.

In the present invention, (I) a vegetable oil component having a predetermined twelfth percentage (%) by weight;

wherein the vegetable oil component is selected from the group consisting of rice bran oil, sunflower oil, olive oil, and combinations thereof.

According to the preferred embodiment of the present invention, the vegetable oil component is obtained by mixing rice bran oil, sunflower oil, and olive oil at a weight ratio of 2:1:1.

In the present invention, (m) a plant powder component having a predetermined thirteenth percentage (%) by weight;

wherein the plant powder component is selected from the group consisting of rice flour, wheat flour, cereal flour, and combinations thereof;

wherein the cereal flour is obtained by mixing five legume seed powders at a weight ratio of 1 part of *Vigna unguiculata* seed powder, 1 part of *Glycine max* seed powder, 1 part of *Vigna radiata* seed powder, 1 part of *Vigna angularis* seed powder, and 1 part of *Phaseolus vulgaris* seed powder.

According to the preferred embodiment of the present invention, the plant powder component is obtained by mixing rice flour, wheat flour, and cereal flour at a weight ratio of 1:1:1.

At step 102, heating the honey component at 65° C.-70° C., adding the royal jelly component, the sugar component and the salt component, then stirring at 500-600 rpm for 45 minutes to obtain a base mixture.

At step 103, mixing the plant powder component with the base mixture at step 102 and stirring at 400-500 rpm for 30 minutes to obtain a first temporary mixture.

At step 104, mixing the components (a) to (g) in order with the first temporary mixture at step 103 to obtain a second temporary mixture, ensuring homogeneous mixing after each addition.

At step 105, mixing the vegetable oil component with the second temporary mixture at step 104 and stirring at 400-500 rpm for 30 minutes to obtain a third temporary mixture.

At step 106, creating a fermented mixture by performing steps (i') to (iii'):

(i') preparing ingredients comprising a substrate mixture and a fermentation microbial mixture;

wherein the substrate mixture is obtained by sterilizing the third temporary mixture at step 105 by autoclaving at 121° C. for 15 minutes;

wherein the fermentation microbial mixture is obtained by mixing a first microbial biomass, a second microbial biomass, a third microbial biomass and a fourth microbial biomass at a weight ratio of 1:1:1:1;

wherein the first microbial biomass is obtained by culturing *Lactobacillus plantarum* (ATCC 14917) on a propagation medium for 24 hours at 37° C., then centrifuging at 4° C. at 6000 rpm for 10 minutes, removing the supernatant and collecting the microbial pellet to obtain the first microbial biomass;

the second microbial biomass is obtained by culturing *Lactobacillus fermentum* (ATCC 23271) on a propagation medium for 24 hours at 37° C., then centrifuging at 4° C. at 6000 rpm for 10 minutes, removing the supernatant and collecting the microbial pellet to obtain the second microbial biomass;

the third microbial biomass is obtained by culturing *Lactobacillus rhamnosus* (ATCC 53103) on a propagation medium for 24 hours at 37° C., then centrifuging at 4° C. at 6000 rpm for 10 minutes, removing the supernatant and collecting the microbial pellet to obtain the third microbial biomass; and the fourth microbial biomass is obtained by culturing *Lactobacillus paracasei* (ATCC 25598) on a propagation medium for 24 hours at 37° C., then centrifuging at 4° C. at 6000 rpm for 10 minutes, removing the supernatant and collecting the microbial pellet to obtain the fourth microbial biomass;

wherein the propagation medium comprises glucose 20 g/L, peptone 10 g/L, yeast extract 5 g/L, $CaCO_3$ 5 g/L, $K_2HPO_4$ 2 g/L, $MgSO_4$ 0.6 g/L, and $MnSO_4$ 0.3 g/L;

(ii') mixing the fermentation microbial mixture with the substrate mixture at a ratio of (1-2):100 w/w, and mixing until homogeneous to obtain a fermentation substrate mixture; and (iii') fermenting the fermentation substrate mixture at 30° C.-35° C. for 40-48 hours to obtain the fermented mixture;

wherein the total viable cell density in the fermented mixture is $1 \times 10^7$ to $1 \times 10^9$ CFU/g.

Finally, at step 107, packaging the fermented mixture at step 106 to obtain the herbal composition for supporting restoration of digestive system function.

One embodiment of the invention provides a herbal composition for supporting restoration of digestive system function 200 ("composition 200"), wherein composition 200 is obtainable by the method 100 and comprises: (a) a *Leucaena leucocephala* extract component having a predetermined first percentage (%) by weight, (b) an eleutherin extract component from *Eleutherine bulbosa* having a predetermined second percentage (%) by weight, (c) an *Andrographis paniculata* extract component having a predetermined third percentage (%) by weight, (d) a *Panax vietnamensis* extract component having a predetermined fourth percentage (%) by weight, (e) a *Pouzolzia zeylanica* extract component having a predetermined fifth percentage (%) by weight, (f) a first herbal mixture extract component having a predetermined sixth percentage (%) by weight, (g) a second herbal mixture extract component having a predetermined seventh percentage (%) by weight, (h) a sugar component having a predetermined eighth percentage (%) by weight, (i) a salt component having a predetermined ninth percentage (%) by weight, (j) a honey component having a predetermined tenth percentage (%) by weight, (k) a royal jelly component having a predetermined eleventh percentage (%) by weight, (l) a vegetable oil component having a predetermined twelfth percentage (%) by weight, and (m) a plant powder component having a predetermined thirteenth percentage (%) by weight.

In the present invention, the predetermined first percentage (%) by weight is 6%-8%, the predetermined second percentage (%) by weight is 4%-6%, the predetermined third percentage (%) by weight is 3%-5%, the predetermined fourth percentage (%) by weight is 6%-8%, the predetermined fifth percentage (%) by weight is 4%-6%, the predetermined sixth percentage (%) by weight is 18%-20%, the predetermined seventh percentage (%) by weight is 12%-14%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

According to the preferred embodiment of the present invention, the predetermined first percentage (%) by weight is 4%-6%, the predetermined second percentage (%) by weight is 4%-6%, the predetermined third percentage (%) by weight is 8%-10%, the predetermined fourth percentage (%) by weight is 6%-8%, the predetermined fifth percentage (%) by weight is 2%-4%, the predetermined sixth percentage (%) by weight is 18%-20%, the predetermined seventh percentage (%) by weight is 10%-12%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

According to the preferred embodiment of the present invention, the predetermined first percentage (%) by weight is 6%-8%, the predetermined second percentage (%) by weight is 4%-5%, the predetermined third percentage (%) by weight is 3%-4%, the predetermined fourth percentage (%) by weight is 6%-8%, the predetermined fifth percentage (%) by weight is 6%-8%, the predetermined sixth percentage (%) by weight is 6%-8%, the predetermined seventh percentage (%) by weight is 12%-14%, the predetermined eighth percentage (%) by weight is 3%-4%, the predetermined ninth percentage (%) by weight is 0.5%-1.5%, the predetermined tenth percentage (%) by weight is 10%-12%, the predetermined eleventh percentage (%) by weight is 10%-12%, the predetermined twelfth percentage (%) by weight is 2%-3%, and the thirteenth percentage (%) by weight is the remainder to make up 100% by weight.

According to the preferred embodiment of the present invention, the predetermined first percentage (%) by weight is 4%-6%, the predetermined second percentage (%) by weight is 5%-6%, the predetermined third percentage (%) by weight is 5%-7%, the predetermined fourth percentage (%) by weight is 14%-16%, the predetermined fifth percentage (%) by weight is 4%-6%, the predetermined sixth percentage (%) by weight is 16%-18%, the predetermined seventh percentage (%) by weight is 8%-10%, the predetermined eighth percentage (%) by weight is 2%-3%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

TABLE 1

Components for preparing composition 200 obtained from method
100 according to an embodiment of the invention

| No. | Component | Percentage (%) | Percentage (%) | Percentage (%) | Percentage (%) |
|-----|-----------|----------------|----------------|----------------|----------------|
| (a) | A *Leucaena leucocephala* extract | 6-8 | 4-6 | 6-8 | 4-6 |
| (b) | An eleutherin extract component from *Eleutherine bulbosa* | 4-6 | 4-6 | 4-5 | 5-6 |
| (c) | An *Andrographis paniculata* extract | 3-5 | 8-10 | 3-4 | 5-7 |
| (d) | A *Panax vietnamensis* extract | 6-8 | 6-8 | 6-8 | 14-16 |

TABLE 1-continued

Components for preparing composition 200 obtained from method
100 according to an embodiment of the invention

| No. | Component | Percentage (%) | Percentage (%) | Percentage (%) | Percentage (%) |
|-----|-----------|----------------|----------------|----------------|----------------|
| (e) | A *Pouzolzia zeylanica* extract | 4-6 | 2-4 | 6-8 | 4-6 |
| (f) | A first herbal mixture extract | 18-20 | 18-20 | 6-8 | 16-18 |
| (g) | A second herbal mixture | 12-14 | 10-12 | 12-14 | 8-10 |
| (h) | A sugar | 4-6 | 4-6 | 3-4 | 2-3 |
| (i) | A salt | 0.5-1.5 | 0.5-1.5 | 0.5-1.5 | 0.5-1.5 |
| (j) | A honey | 8-10 | 8-10 | 10-12 | 8-10 |
| (k) | A royal jelly | 8-10 | 8-10 | 10-12 | 8-10 |
| (l) | A vegetable oil | 2-3 | 2-3 | 2-3 | 2-3 |
| (m) | A plant powder | Remaining percent | Remaining percent | Remaining percent | Remaining percent |

TABLE 2

List of herbal materials in Vietnam according to an embodiment of the invention

| No. | Name | Part used | Active constituents | Pharmacological effects | Distribution |
|-----|------|-----------|---------------------|-------------------------|--------------|
| 1 | *Leucaena leucocephala* | Root, stem, seed | Alkaloids, tannins, flavonoids | Antimicrobial and antiparasitic; anti-inflammatory | Vietnam |
| 2 | *Eleutherine bulbosa* | Bulb | Quinones (eleutherin, isoeleutherin); tannins | Antibacterial in the intestinal tract; detoxification; treatment of poor appetite, dyspepsia and abdominal bloating | Vietnam |
| 3 | *Andrographis paniculata* | Leaves | Diterpene lactones | Treatment of enteritis, dysentery, abdominal pain with diarrhea; acute gastritis | Northern Vietnam |
| 4 | *Panax vietnamensis* | Root, stem, leaves | Triterpenoid saponins | Reduction of stress-induced gastric ulcers; stimulation of digestion; general tonic/body restoration | Ngoc Linh mountain area (Kon Tum, Quang Nam) |
| 5 | *Pouzolzia zeylanica* | Stem, leaves | Flavonoids | Supportive treatment for dysentery, enteritis and stomach pain | Vietnam |
| 6 | *Curcuma zedoaria* | Root | Essential oil (curzerenone), curcuminoids | Supports treatment of dyspeptic symptoms, bloating and nausea | Vietnam |
| 7 | *Curcuma longa* | Root | Curcumin, essential oil (zingiberene) | Anti-inflammatory; promotes healing of gastric and duodenal ulcers | Vietnam |
| 8 | *Zingiber officinale* | Root | Essential oil (zingiberene), gingerol, shogaol | Supports treatment of nausea and vomiting, diarrhea, bloating; stimulates digestion | Vietnam |
| 9 | *Alpinia galanga* | Root | Essential oil (cineole), flavonoids (galangin) | Analgesic; supports treatment of stomach pain due to cold, nausea, vomiting, diarrhea | Vietnam |
| 10 | *Platycodon grandiflorus* | Root | Saponins (platycodin A, C, D) | Supports treatment of dysentery and abdominal pain | Northern Vietnam (Highland regions) |
| 11 | *Citrus aurantium* | Fruit | Flavonoids (hesperidin), essential oil, synephrine | Supports treatment of stomach pain, bloating and constipation | Northern and Central Vietnam |
| 12 | *Plumbago zeylanica* | Stem | Plumbagin, Flavonoids | Stimulates digestion; supports treatment of constipation and poor appetite/dyspepsia | Southern and Central Vietnam |
| 13 | *Cleistocalyx operculatus* | Leaves | Tannins; essential oil; flavonoids | Supports treatment of chronic colitis, abdominal bloating and diarrhea | Northern and Central Vietnam |

TABLE 2-continued

List of herbal materials in Vietnam according to an embodiment of the invention

| No. | Name | Part used | Active constituents | Pharmacological effects | Distribution |
|---|---|---|---|---|---|
| 14 | *Ampelopsis cantoniensis* | Leaves | Flavonoids (myricetin); tannins | Antibacterial; supports treatment of gastric and duodenal ulcers | Northern Vietnam (Highland regions) |
| 15 | *Lycopodiella cernua* | Whole plant (root, stem, leaves) | Alkaloids (huperzine A, lycopodine) | Anti-inflammatory; supports treatment of gastric and duodenal ulcers | Northern and Central Vietnam (Highland regions) |
| 16 | *Ficus carica* | Fruit | Flavonoids, polyphenols | Supports treatment of digestive disorders and constipation | Vietnam |

According to another embodiment of the invention, composition 200 obtained by method 100 for supporting restoration of digestive system function is used by dissolving the composition in water to obtain a solution and administering the solution orally to a subject in need thereof.

In the present invention, composition 200 obtained by method 100 meets the organoleptic and safety specifications listed in Tables 3 and 4 below.

TABLE 3

Organoleptic specifications of composition 200 obtained by method 100 according to an embodiment of the invention

| No. | Parameter | Composition 200 |
|---|---|---|
| 1 | Physical form | Viscous concentrated form |
| 2 | Color | Dark brown |
| 3 | Taste | Characteristic aroma and taste derived from the blended components |
| 4 | Ash content | 4%-6% |

TABLE 4

Safety criteria of composition 200 obtained from method 100 according to an embodiment of the invention

| No. | Parameter | Result |
|---|---|---|
| 1 | Arsenic (As) | Not detected (LOD = 0, 12 ppm) |
| 2 | Cadmium (Cd) | Not detected (LOD = 0, 06 ppm) |
| 3 | Lead (Pb) | Not detected (LOD = 0, 12 ppm) |
| 4 | Mercury (Hg) | Not detected (LOD = 0, 06 ppm) |
| 5 | Total yeasts and molds | <10 CFU/g |
| 6 | Coliforms/0.1 g | Not detected |
| 7 | *Escherichia coli*/0.1 g | Not detected |
| 8 | *Salmonella*/0.1 g | Not detected |

The method of the invention enables effective integration of raw material processing, extraction of bioactive compounds, and microbial fermentation into a unified process with clearly controlled operating conditions and defined blending ratios. As a result, the method ensures high reproducibility, facilitates standardization, and is suitable for scale-up to industrial production, while improving the recovery efficiency of bioactive compounds, stabilizing product quality, and ensuring microbiological safety during manufacturing.

The resulting herbal composition exhibits high biological effectiveness in supporting restoration of digestive system function, stabilizing and rebalancing the intestinal microbiota, and improving digestion and nutrient absorption. In addition, the composition contributes to improving physical condition, enhancing overall health, supporting blood glucose stabilization, and is particularly suitable for individuals at risk of impaired digestive function or experiencing common digestive disorders.

EXAMPLES

The purpose of the following examples is to demonstrate that the technical solutions of the present invention have been studied and successfully tested by the inventor. In particular, composition 200 obtained by method 100 comprises four examples listed in Table 5 below according to an embodiment of the invention. Specifically:

TABLE 5

Blended components according to embodiments of the invention

| No. | Component | Example 1 | Example 2 | Example 3 | Example 4 |
|---|---|---|---|---|---|
| (a) | A *Leucaena leucocephala* extract | 70 kg | 50 kg | 70 kg | 50 kg |
| (b) | An eleutherin extract component from *Eleutherine bulbosa* | 50 kg | 50 kg | 45 kg | 55 kg |
| (c) | An *Andrographis paniculata* extract | 40 kg | 90 kg | 35 kg | 60 kg |
| (d) | A *Panax vietnamensis* extract | 70 kg | 70 kg | 70 kg | 150 kg |
| (e) | A *Pouzolzia zeylanica* extract | 50 kg | 30 kg | 70 kg | 50 kg |
| (f) | A first herbal mixture extract | 190 kg | 190 kg | 70 kg | 170 kg |
| (g) | A second herbal mixture | 130 kg | 110 kg | 110 kg | 90 kg |
| (h) | A sugar | 50 kg | 50 kg | 35 kg | 25 kg |
| (i) | A salt | 10 kg | 10 kg | 10 kg | 10 kg |
| (j) | A honey | 90 kg | 90 kg | 110 kg | 90 kg |
| (k) | A royal jelly | 90 kg | 90 kg | 110 kg | 90 kg |
| (l) | A vegetable oil | 25 kg | 25 kg | 25 kg | 25 kg |
| (m) | A plant powder | 135 kg | 145 kg | 240 kg | 135 kg |

Example 1

Preparation of composition 200 by method 100, comprising the following steps:

(I) preparing components comprising components (a)-(m) in the amounts listed in the Example 1 column of Table 5 above;

(II) heating the honey component at 65° C.-70° C., adding the royal jelly component, the sugar component and the salt component, then stirring at 500-600 rpm for 45 minutes to obtain a base mixture;

(III) mixing the plant powder component with the base mixture obtained in step (II) and stirring at 400-500 rpm for 30 minutes to obtain a first temporary mixture;

(IV) mixing the components (a)-(g) in order with the first temporary mixture at step (III) to obtain a second temporary mixture, ensuring homogeneous mixing after each addition;

(V) mixing the vegetable oil component with the second temporary mixture at step (IV) and stirring at 400-500 rpm for 30 minutes to obtain a third temporary mixture;

(VI) creating a fermented mixture by performing steps (i') to (iii'):

(i') preparing ingredients comprising a substrate mixture and a fermentation microbial mixture;

wherein the substrate mixture is obtained by sterilizing the third temporary mixture at step (v) by autoclaving at 121° C. for 15 minutes;

wherein the fermentation microbial mixture is obtained by mixing a first microbial biomass, a second microbial biomass, a third microbial biomass and a fourth microbial biomass at a weight ratio of 1:1:1:1; wherein the first microbial biomass is obtained by culturing *Lactobacillus plantarum* (ATCC 14917) on a propagation medium for 24 hours at 37° C., then centrifuging at 4° C. at 6000 rpm for 10 minutes, removing the supernatant and collecting the microbial pellet to obtain the first microbial biomass;

the second microbial biomass is obtained by culturing *Lactobacillus fermentum* (ATCC 23271) on a propagation medium for 24 hours at 37° C., then centrifuging at 4° C. at 6000 rpm for 10 minutes, removing the supernatant and collecting the microbial pellet to obtain the second microbial biomass;

the third microbial biomass is obtained by culturing *Lactobacillus rhamnosus* (ATCC 53103) on a propagation medium for 24 hours at 37° C., then centrifuging at 4° C. at 6000 rpm for 10 minutes, removing the supernatant and collecting the microbial pellet to obtain the third microbial biomass; and the fourth microbial biomass is obtained by culturing *Lactobacillus paracasei* (ATCC 25598) on a propagation medium for 24 hours at 37° C., then centrifuging at 4° C. at 6000 rpm for 10 minutes, removing the supernatant and collecting the microbial pellet to obtain the fourth microbial biomass;

wherein the propagation medium comprises glucose 20 g/L, peptone 10 g/L, yeast extract 5 g/L, $CaCO_3$ 5 g/L, $K_2HPO_4$ 2 g/L, $MgSO_4$ 0.6 g/L, and $MnSO_4$ 0.3 g/L;

(ii') mixing the fermentation microbial mixture with the substrate mixture at a ratio of (1-2):100 w/w, and mixing until homogeneous to obtain a fermentation substrate mixture; and (iii') fermenting the fermentation substrate mixture at 30° C.-35° C. for 40-48 hours to obtain the fermented mixture;

wherein the total viable cell density in the fermented mixture is $1×10^7$ to $1×10^9$ CFU/g; and (VII) packaging the fermented mixture at step (VI) to obtain the herbal composition for supporting restoration of digestive system function.

Example 2

Preparation of composition 300 by method 100, carried out in the same manner as described in Example 1 above and comprising steps (I) to (VII), except that at step (I), the preparation of ingredients comprises components (a)-(m) in the amounts listed in the Example 2 column of Table 5 above.

Example 3

Preparation of composition 400 by method 100, carried out in the same manner as described in Example 1 above and comprising steps (I) to (VII), except that at step (I), the preparation of ingredients comprises components (a)-(m) in the amounts listed in the Example 3 column of Table 5 above.

Example 4

Preparation of composition 500 by method 100, carried out in the same manner as described in Example 1 above and comprising steps (I) to (VII), except that at step (I) the preparation of ingredients comprises components (a)-(m) in the amounts listed in the Example 4 column of Table 5 above.

Example 5

Evaluation of anti-gastroesophageal reflux activity of compositions obtained according to exemplary embodiments of the invention

(I) Materials and Methods

Experimental animals:

Wistar rats of both sexes, healthy, weighing 180-220 g. The animals were acclimatized for 7 days prior to the study and maintained throughout the experimental period under laboratory conditions with free access to food and water.

Test subjects: Composition 200 obtained from Example 1, composition 300 obtained from Example 2, composition 400 obtained from Example 3, and composition 500 obtained from Example 4.

Experimental method: The rats were randomly divided into 11 groups (each group comprising 9 animals):

Group 1 (biological control): administered distilled water at a dose of 10 mL/kg;

Group 2 (model group): administered distilled water at a dose of 10 ml/kg in combination with indomethacin at a dose of 10 mg/kg;

Group 3 (positive control): administered esomeprazole at a dose of 10 mg/kg in combination with indomethacin at a dose of 10 mg/kg;

Group 4 (composition 200, low dose): administered composition 200 at a dose of 0.25 g/kg in combination with indomethacin at a dose of 10 mg/kg;

Group 5 (composition 200, high dose): administered composition 200 at a dose of 0.75 g/kg in combination with indomethacin at a dose of 10 mg/kg;

Group 6 (composition 300, low dose): administered composition 300 at a dose of 0.25 g/kg in combination with indomethacin at a dose of 10 mg/kg;

Group 7 (composition 300, high dose): administered composition 300 at a dose of 0.75 g/kg in combination with indomethacin at a dose of 10 mg/kg;

Group 8 (composition 400, low dose): administered composition 400 at a dose of 0.25 g/kg in combination with indomethacin at a dose of 10 mg/kg;

Group 9 (composition 400, high dose): administered composition 400 at a dose of 0.75 g/kg in combination with indomethacin at a dose of 10 mg/kg;

Group 10 (composition 500, low dose): administered composition 500 at a dose of 0.25 g/kg in combination with indomethacin at a dose of 10 mg/kg; and Group 11 (composition 500, high dose): administered composition 500 at a dose of 0.75 g/kg in combination with indomethacin at a dose of 10 mg/kg.

Animals in each group were administered distilled water or the respective test substances once daily in the morning for 7 consecutive days. On day 7 of the study, one hour after administration of distilled water or the test substance, indomethacin was administered. Rats in Groups 2 to 11 were subjected to induction of a gastroesophageal reflux model by laparotomy and ligation of the stomach at two sites: a first site at the junction between the fundus and the body of the stomach, and a second site at the pylorus. The abdominal cavity was closed, and after 6 hours the animals were anesthetized, and the esophagus and stomach were exposed.

Gastric contents were collected into graduated centrifuge tubes to measure volume, pH, free acidity, and total acidity of the gastric juice. The gastrointestinal tract from the esophagus to the stomach was excised, the esophagus and stomach were opened along the greater curvature using scissors, rinsed with cold physiological saline, and the esophagus and stomach were fixed for further evaluation.

Evaluation parameters:

Gastric juice volume: calculated per 100 g of body weight, and the mean value of each group was used for comparison.

Gastric juice pH: measured using a pH meter.

Determination of free acidity and total acidity of the gastric juice.

Esophageal ulcer index: esophageal ulceration was scored as follows:

0 points when no lesions were observed;

1 point when a few minor lesions or hemorrhagic spots were observed;

2 points when the total ulcerated area was less than 30 mm$^2$;

3 points when the total ulcerated area was equal to or greater than 30 mm$^2$; and 4 points when perforation of the esophagus was observed.

Ulcer inhibition rate: calculated according to the following formula:

$$I(\%) = \frac{AC - AT}{AC} \times 100(\%)$$

wherein:

I (%) represents the percentage of ulcer inhibition;

AC represents the mean ulcerated esophageal mucosal area of rats in the model group; and AT represents the mean ulcerated esophageal mucosal area of rats in the test sample group.

(II) Results

TABLE 6

Effects of the tested compositions on gastric juice volume, gastric juice pH, free acidity, and total acidity

| Experimental group (n = 9) | Gastric juice volume (mL/100 g rat) | Gastric juice pH | Free acidity (mEq/L) | Total acidity (mEq/L) |
|---|---|---|---|---|
| Biological control | 0.20 ± 0.06 | 2.70 ± 0.60 | 17.0 ± 5.0 | 42.0 ± 13.0 |
| Model group | 1.80 ± 0.45 | 2.05 ± 0.40 | 24.0 ± 4.8 | 55.0 ± 11.0 |
| Positive control (Esomeprazole 10 mg/kg) | 1.38 ± 0.33 | 3.75 ± 0.90 | 13.1 ± 3.4 | 32.0 ± 9.2 |
| Composition 200, low dose (0.25 g/kg) | 1.50 ± 0.45 | 3.25 ± 0.80 | 16.0 ± 4.5 | 38.5 ± 8.5 |
| Composition 200, high dose (0.75 g/kg) | 1.18 ± 0.32 | 3.90 ± 0.65 | 11.6 ± 3.0 | 29.8 ± 6.8 |
| Composition 300, low dose (0.25 g/kg) | 1.62 ± 0.48 | 3.05 ± 0.92 | 20.8 ± 5.6 | 44.0 ± 9.6 |
| Composition 300, high dose (0.75 g/kg) | 1.42 ± 0.40 | 3.30 ± 0.85 | 17.5 ± 4.2 | 37.2 ± 8.0 |
| Composition 400, low dose (0.25 g/kg) | 1.58 ± 0.47 | 3.10 ± 0.88 | 19.2 ± 5.0 | 41.0 ± 9.0 |
| Composition 400, high dose (0.75 g/kg) | 1.30 ± 0.38 | 3.50 ± 0.78 | 15.7 ± 4.0 | 35.4 ± 8.1 |
| Composition 500, low dose (0.25 g/kg) | 1.66 ± 0.49 | 3.12 ± 0.90 | 18.9 ± 5.1 | 40.2 ± 9.3 |
| Composition 500, high dose (0.75 g/kg) | 1.36 ± 0.39 | 3.40 ± 0.82 | 14.9 ± 3.8 | 34.6 ± 8.0 |

Based on Table 6, the reflux model group (n=9) exhibited a pronounced increase in gastric secretion and an acidic environment, as indicated by a gastric juice volume of 1.80±0.45 mL/100 g, a pH of 2.05±0.40, free acidity of 24.0±4.8 mEq/L, and total acidity of 55.0±11.0 mEq/L. The positive control markedly improved these parameters, showing a gastric juice volume of 1.38±0.33 mL/100 g, a pH of 3.75±0.90, and a total acidity of 32.0±9.2 mEq/L.

All tested compositions demonstrated a general trend toward reducing gastric juice volume, increasing pH, and decreasing acidity relative to the model group, although the magnitude of the effects differed among the compositions and between the low-dose and high-dose regimens. In particular, Composition 200 at the high dose achieved a pH of 3.90±0.65, a total acidity of 29.8±6.8 mEq/L, and a gastric juice volume of 1.18±0.32 mL/100 g, which were comparable to those observed in the positive control group. Compositions 300, 400, and 500 at the high dose also reduced acidity and increased pH; however, their effects were less pronounced than those observed for Composition 200 at the high dose.

TABLE 7

| Experimental group (n = 9) | Mean ulcer area (mm$^2$) | Esophageal index | Ulcer reduction rate (%) |
|---|---|---|---|
| Biological control | 0.0 ± 0.0 | 0.00 ± 0.00 | — |
| Model group | 12.2 ± 1.2 | 1.78 ± 0.25 | — |
| Positive control (Esomeprazole 10 mg/kg) | 1.2 ± 0.8 | 0.89 ± 0.15 | 90.2 |
| Composition 200, low dose (0.25 g/kg) | 4.6 ± 1.0 | 1.05 ± 0.22 | 62.3 |
| Composition 200, high dose (0.75 g/kg) | 0.7 ± 0.6 | 0.70 ± 0.12 | 94.3 |
| Composition 300, low dose (0.25 g/kg) | 8.0 ± 1.3 | 1.02 ± 0.20 | 34.4 |
| Composition 300, high dose (0.75 g/kg) | 3.8 ± 1.1 | 0.88 ± 0.18 | 68.9 |
| Composition 400, low dose (0.25 g/kg) | 6.5 ± 1.2 | 1.12 ± 0.26 | 46.7 |
| Composition 400, high dose (0.75 g/kg) | 2.9 ± 0.9 | 0.95 ± 0.20 | 76.2 |
| Composition 500, low dose (0.25 g/kg) | 5.4 ± 1.1 | 1.20 ± 0.28 | 55.7 |
| Composition 500, high dose (0.75 g/kg) | 2.2 ± 0.9 | 0.88 ± 0.18 | 82 |

Table 7: Effects of the tested compositions on esophageal ulcer lesions

Based on Table 7, the ulcer-induced model produced pronounced esophageal damage, with a mean ulcer area of 12.2±1.2 mm$^2$ and an esophageal index of 1.78±0.25, whereas no lesions were observed in the biological control group. The positive control group treated with esomeprazole markedly reduced the severity of ulceration, as evidenced by a mean ulcer area of 1.2±0.8 mm$^2$ and an ulcer reduction rate of 90.2%, thereby confirming the suitability of the experimental model.

All tested compositions demonstrated a capacity to reduce esophageal injury relative to the model group, with varying degrees of effectiveness among different formulations and dose levels. Notably, Composition 200 at the high dose exhibited a pronounced protective effect, with a mean ulcer area of only 0.7±0.6 mm$^2$, an esophageal index of 0.70±0.12, and an ulcer reduction rate of 94.3%, which was comparable to or slightly higher than that observed for esomeprazole in this dataset. At the low dose, Composition 200 still showed substantial efficacy, with a mean ulcer area of 4.6±1.0 mm$^2$ and an ulcer reduction rate of 62.3%.

The other compositions also exhibited mucosal protective effects to varying extents, with mean ulcer areas ranging from 2.2±0.9 to 8.0±1.3 mm$^2$ and corresponding ulcer reduction rates from 34.4% to 82.0%, indicating a dose-dependent trend that was not uniform across all formulations.

Example 6

Evaluation of the anti-gastric and duodenal ulcer effects of the compositions obtained according to exemplary embodiments of the invention Materials and Methods Experimental animals:
Wistar albino rats of both sexes, healthy, weighing 180-220 g. The rats were acclimatized for 7 days prior to the experiment and maintained throughout the study under laboratory conditions with free access to food and water.
Test materials: Composition 200 obtained from Example 1, Composition 300 obtained from Example 2, Composition 400 obtained from Example 3, and Composition 500 obtained from Example 4.
Experimental method: The rats were randomly divided into eleven groups, each group consisting of nine animals, as follows:
Group 1 (biological control): orally administered distilled water at a dose of 10 mL/kg;
Group 2 (model): orally administered distilled water at a dose of 10 mL/kg in combination with cysteamine at a dose of 400 mg/kg;
Group 3 (positive control): orally administered ranitidine at a dose of 50 mg/kg in combination with cysteamine at a dose of 400 mg/kg;
Group 4 (Composition 200, low dose): orally administered Composition 200 at a dose of 0.25 g/kg in combination with cysteamine at a dose of 400 mg/kg;
Group 5 (Composition 200, high dose): orally administered Composition 200 at a dose of 0.75 g/kg in combination with cysteamine at a dose of 400 mg/kg;
Group 6 (Composition 300, low dose): orally administered Composition 300 at a dose of 0.25 g/kg in combination with cysteamine at a dose of 400 mg/kg;
Group 7 (Composition 300, high dose): orally administered Composition 300 at a dose of 0.75 g/kg in combination with cysteamine at a dose of 400 mg/kg;
Group 8 (Composition 400, low dose): orally administered Composition 400 at a dose of 0.25 g/kg in combination with cysteamine at a dose of 400 mg/kg;
Group 9 (Composition 400, high dose): orally administered Composition 400 at a dose of 0.75 g/kg in combination with cysteamine at a dose of 400 mg/kg;
Group 10 (Composition 500, low dose): orally administered Composition 500 at a dose of 0.25 g/kg in combination with cysteamine at a dose of 400 mg/kg; and
Group 11 (Composition 500, high dose): orally administered Composition 500 at a dose of 0.75 g/kg in combination with cysteamine at a dose of 400 mg/kg.
The rats were orally administered distilled water or the test substances once daily in the morning for a continuous period of 7 days. On day 7 of the experiment, one hour after administration of distilled water or the test substances, gastric and duodenal ulcers were induced in rats of Groups 2 to 11 by orally administering cysteamine at a dose of 400 mg/kg twice, with an interval of 4 hours between administrations. The rats were fasted for 18 hours prior to cysteamine administration.
At 24 hours after the final cysteamine administration, the rats were sacrificed by laparotomy, and the stomach was exposed. The gastrointestinal tract from the distal esophagus adjacent to the cardia to the duodenum at a distance of 5 cm from the pylorus was excised separately. The ulcerated surfaces were treated with 5% formaldehyde and the specimens were fixed. Ulcer lesions were observed using a magnifying glass at 10× magnification and graded according to the following criteria:
Grade I lesions: edema, congestion, and petechial hemorrhages beneath the mucosa;

Grade II lesions: submucosal hemorrhage and superficial mucosal lesions; Grade III lesions: deep ulcers and invasive lesions.

Evaluation parameters included:

the percentage of rats presenting gastric and duodenal ulcers in each group;

the mean number of ulcer lesions per group; and the ulcer index (UI), calculated according to the following formula:

$$UI = (\text{number of Grade I lesions}) \times 1 + (\text{number of Grade II lesions}) \times 2 + (\text{number of Grade III lesions}) \times 3$$

(II) Results

TABLE 8

Effects of the tested compositions on the percentage of rats with gastric-duodenal ulcers, the number of ulcer lesions, and the mean ulcer index

| Experimental group (n = 9) | Percentage of rats with gastric-duodenal ulcers (%) | Number of ulcer lesions | Mean ulcer index |
|---|---|---|---|
| Biological control | 0.0 ± 0.0 | 0.0 ± 0.0 | 0.0 ± 0.0 |
| Model group | 100 | 7.2 ± 2.3 | 16.5 ± 6.5 |
| Positive control (Ranitidine 50 mg/kg) | 66.7 | 2.5 ± 1.8 | 5.6 ± 4.2 |
| Composition 200, low dose (0.25 g/kg) | 100 | 5.5 ± 1.4 | 10.8 ± 3.6 |
| Composition 200, high dose (0.75 g/kg) | 88.9 | 3.8 ± 1.0 | 7.0 ± 2.4 |
| Composition 300, low dose (0.25 g/kg) | 100 | 4.0 ± 1.1 | 8.5 ± 3.0 |
| Composition 300, high dose (0.75 g/kg) | 55.6 | 1.5 ± 0.8 | 3.2 ± 1.9 |
| Composition 400, low dose (0.25 g/kg) | 88.9 | 3.2 ± 1.0 | 6.8 ± 2.5 |
| Composition 400, high dose (0.75 g/kg) | 66.7 | 2.8 ± 0.9 | 5.0 ± 2.0 |
| Composition 500, low dose (0.25 g/kg) | 100 | 4.5 ± 1.2 | 9.0 ± 3.4 |
| Composition 500, high dose (0.75 g/kg) | 77.8 | 2.9 ± 1.0 | 6.5 ± 2.3 |

Based on Table 8, the cysteamine-induced ulcer model produced pronounced gastric-duodenal injury, with the percentage of rats presenting ulcers reaching 100%, a mean number of ulcer lesions of 7.2±2.3, and a mean ulcer index of 16.5±6.5, whereas no lesions were observed in the biological control group. The ranitidine positive control exhibited a clear protective effect, with the percentage of rats with ulcers reduced to 66.7%, a mean number of ulcer lesions of 2.5±1.8, and an ulcer index of 5.6±4.2, thereby confirming the validity of the experimental model. All tested compositions reduced ulcer severity compared with the model group and showed a dose-dependent trend. Notably, composition 300 at the high dose demonstrated superior efficacy, with the percentage of rats with ulcers decreased to 55.6%, a mean number of ulcer lesions of only 1.5±0.8, and an ulcer index of 3.2±1.9, which were lower than those of the positive control in this dataset. The remaining compositions also exhibited mucosal protective effects to varying extents, with mean numbers of ulcer lesions ranging from 2.8±0.9 to 5.5±1.4 and ulcer indices ranging from 5.0±2.0 to 10.8±3.6.

Example 7

Evaluation of the supportive effect in reducing irritable bowel syndrome of the compositions obtained according to exemplary embodiments of the invention Materials and Methods Experimental animals:

Wistar albino rats of both sexes, healthy, weighing 180-220 g. The rats were acclimatized for 7 days prior to the experiment and maintained throughout the study under laboratory conditions with free access to food and water.

Test materials: Composition 200 obtained from Example 1, composition 300 obtained from Example 2, composition 400 obtained from Example 3, and composition 500 obtained from Example 4.

Experimental design:

The rats were randomly divided into 12 groups (n=9 per group):

Group 1 (biological control): administered distilled water daily;

Group 2 (ethanol control): administered distilled water daily;

Group 3 (model group): administered distilled water daily;

Group 4 (positive control): administered mebeverine at a dose of 80 mg/kg;

Group 5 (composition 200, low dose): administered composition 200 at a dose of 0.25 g/kg;

Group 6 (composition 200, high dose): administered composition 200 at a dose of 0.75 g/kg;

Group 7 (composition 300, low dose): administered composition 300 at a dose of 0.25 g/kg;

Group 8 (composition 300, high dose): administered composition 300 at a dose of 0.75 g/kg;

Group 9 (composition 400, low dose): administered composition 400 at a dose of 0.25 g/kg;

Group 10 (composition 400, high dose): administered composition 400 at a dose of 0.75 g/kg;

Group 11 (composition 500, low dose): administered composition 500 at a dose of 0.25 g/kg; and Group 12 (composition 500, high dose): administered composition 500 at a dose of 0.75 g/kg.

The rats were orally administered distilled water or the corresponding test substances once daily in the morning. On day 7, the rats were anesthetized and the irritable bowel syndrome (IBS) model was induced as follows: rats in Groups 3 to 12 received an intracolonic administration of 100 µL of a 2% mustard oil solution prepared in 30% ethanol, while rats in Groups 1 and 2 received physiological saline or 30% ethanol as the corresponding vehicle controls. The mustard oil solution, saline, or ethanol was administered at a position 4 cm from the anus. After model induction, the rats continued to receive water or the corresponding test substances for an additional 20 days.

Evaluation parameters:

Twenty-four hours after the final administration of water or test substances, the following parameters were evaluated in the protective and recovery models:

Colon weight (g);

Colon length (cm);

Fecal condition score;

Inflammation score; and

Histopathological (microscopic) score.

(II) Results

TABLE 9

Effects of the experimental compositions on macroscopic and
microscopic colon parameters in the protective model

| Experimental group (n = 9) | Colon weight (g) | Colon length (cm) | Stool condition score | Inflammation score | Histological score |
|---|---|---|---|---|---|
| Biological control | 0.42 ± 0.09 | 9.10 ± 0.85 | 0.20 ± 0.30 | 0.12 ± 0.18 | 0.05 ± 0.07 |
| Ethanol control | 0.60 ± 0.10 | 8.50 ± 1.00 | 0.95 ± 1.05 | 0.40 ± 0.45 | 0.15 ± 0.30 |
| Model group | 0.62 ± 0.11 | 8.30 ± 1.05 | 1.10 ± 1.20 | 0.45 ± 0.50 | 0.18 ± 0.40 |
| Positive control (Mebeverine 80 mg/kg) | 0.48 ± 0.09 | 8.95 ± 1.00 | 0.40 ± 0.50 | 0.25 ± 0.35 | 0.10 ± 0.15 |
| Composition 200, low dose (0.25 g/kg) | 0.58 ± 0.10 | 8.65 ± 1.08 | 0.85 ± 0.95 | 0.38 ± 0.45 | 0.14 ± 0.22 |
| Composition 200, high dose (0.75 g/kg) | 0.50 ± 0.08 | 8.90 ± 0.98 | 0.52 ± 0.60 | 0.28 ± 0.32 | 0.11 ± 0.16 |
| Composition 300, low dose (0.25 g/kg) | 0.60 ± 0.10 | 8.50 ± 1.06 | 0.95 ± 1.05 | 0.40 ± 0.48 | 0.16 ± 0.30 |
| Composition 300, high dose (0.75 g/kg) | 0.49 ± 0.08 | 8.98 ± 0.96 | 0.48 ± 0.55 | 0.26 ± 0.30 | 0.09 ± 0.14 |
| Composition 400, low dose (0.25 g/kg) | 0.56 ± 0.09 | 8.72 ± 1.02 | 0.72 ± 0.82 | 0.33 ± 0.40 | 0.13 ± 0.20 |
| Composition 400, high dose (0.75 g/kg) | 0.46 ± 0.07 | 9.05 ± 0.90 | 0.30 ± 0.42 | 0.18 ± 0.25 | 0.07 ± 0.10 |
| Composition 500, low dose (0.25 g/kg) | 0.59 ± 0.11 | 8.60 ± 1.10 | 0.88 ± 1.00 | 0.39 ± 0.46 | 0.15 ± 0.28 |
| Composition 500, high dose (0.75 g/kg) | 0.52 ± 0.09 | 8.92 ± 0.98 | 0.50 ± 0.60 | 0.27 ± 0.33 | 0.10 ± 0.15 |

Based on Table 9, the irritable bowel syndrome model exhibited marked alterations compared with the biological control group, including an increase in colon weight from 0.42±0.09 g to 0.62±0.11 g, a reduction in colon length from 9.10±0.85 cm to 8.30±1.05 cm, an increase in the stool condition score to 1.10±1.20, and an increase in the histological score to 0.18±0.40.

All experimental compositions improved several parameters relative to the model group. In particular, composition 200 at the high dose reduced the stool condition score to 0.52±0.60 and the inflammation score to 0.28±0.32, while composition 300 at the high dose achieved corresponding values of 0.48±0.55 and 0.26±0.30.

Notably, composition 400 at the high dose exhibited the most pronounced effect, with a colon weight of 0.46±0.07 g, a colon length of 9.05±0.90 cm, a stool condition score of 0.30±0.42, and a histological score of 0.07±0.10. These values were close to those of the biological control group and were substantially lower than those observed in the model group.

Example 8

Evaluation of the blood-glucose lowering effect of the compositions obtained according to exemplary embodiments of the invention Materials and Methods Experimental animals: Male Swiss albino mice, 5-6 weeks old, were used. Animals were fed a standard pelleted diet formulated for laboratory rodents and stabilized for one week prior to the experiment.

Streptozotocin (STZ) hyperglycemia model: Hyperglycemia was induced by a single intraperitoneal injection of streptozotocin (STZ) prepared in sodium citrate buffer (pH 4.5) at a dose of 170 mg/kg body weight (designated STZ+). Seven days after STZ injection, tail-vein blood samples were collected to assess blood glucose. Animals with fasting blood glucose values (after at least 12 hours fasting)≥126 mg/dL were selected for the glucose-lowering study.

Experimental design and treatment groups: The animals were allocated into two sets with each group containing 6-8 mice. Oral dosing volume was 10 mL/kg once daily. The STZ+ groups received one of the following by oral administration: distilled water (vehicle), Composition 200 low dose (0.25 g/kg), Composition 200 high dose (0.75 g/kg), Composition 300 low dose (0.25 g/kg), Composition 300 high dose (0.75 g/kg), Composition 400 low dose (0.25 g/kg), Composition 400 high dose (0.75 g/kg), Composition 500 low dose (0.25 g/kg), Composition 500 high dose (0.75 g/kg), or the reference drug glibenclamide at 5 mg/kg as a single dose. Treatments were administered once daily for 7 days. A parallel set of normal control animals (STZ−) was arranged in an analogous manner.

Endpoints in the STZ hyperglycemia experiment: Blood glucose concentration was measured at two time points for each experimental group: on day 1 of the experiment before the first oral administration and on day 7 one hour after the final oral administration of distilled water, the test compositions (Compositions 200, 300, 400 and 500 at both low and high doses), or the reference drug.

Endpoints in the glucose tolerance test: On day 7, one hour after the final oral administration of distilled water, Composition 500 low dose, Composition 500 high dose, or the reference drug, an oral glucose tolerance test (OGTT) was performed by administering an oral glucose load of 2 g/kg. Tail-vein blood samples were collected to determine blood glucose at 30 minutes after glucose administration. For the STZ+ groups, blood glucose was determined at 30 minutes and 120 minutes after the glucose load.

(II) Results

TABLE 10

Effects of the tested compositions on fasting blood glucose before and after treatment

| | Blood glucose concentration (mg/dL) | |
|---|---|---|
| Experimental group | Before treatment | After 7 days treatment |
| Normal control (STZ−) | 92.0 ± 4.0 | 90.5 ± 4.5 |
| Disease control (STZ+) | 159.2 ± 12.8 | 184.6 ± 14.2 |
| Glibenclamide (5 mg/kg) | 158.0 ± 13.5 | 98.2 ± 8.4 |
| Composition 200, low dose (0.25 g/kg) | 160.5 ± 14.1 | 142.3 ± 12.0 |
| Composition 200, high dose (0.75 g/kg) | 161.4 ± 13.8 | 120.7 ± 10.5 |
| Composition 300, low dose (0.25 g/kg) | 159.8 ± 13.9 | 138.6 ± 11.9 |
| Composition 300, high dose (0.75 g/kg) | 162.0 ± 14.2 | 115.8 ± 10.2 |
| Composition 400, low dose (0.25 g/kg) | 161.0 ± 14.0 | 130.9 ± 11.4 |
| Composition 400, high dose (0.75 g/kg) | 160.8 ± 13.7 | 109.9 ± 9.6 |
| Composition 500, low dose (0.25 g/kg) | 162.2 ± 14.5 | 125.4 ± 10.8 |
| Composition 500, high dose (0.75 g/kg) | 163.5 ± 15.0 | 95.6 ± 8.1 |

Based on Table 10, the streptozotocin-induced hyperglycemia model produced a marked increase in fasting blood glucose compared with the physiological control group, with a value after 7 days of 184.6±14.2 mg/dL versus 90.5±4.5 mg/dL in the STZ− group, indicating successful model establishment. The positive control glibenclamide substantially reduced fasting glucose from 158.0±13.5 mg/dL to 98.2±8.4 mg/dL after 7 days of treatment.

All tested compositions showed a tendency to lower blood glucose relative to the disease control group, with dose-dependent effects. At the low dose, post-treatment glucose values ranged from 130.9±11.4 to 142.3±12.0 mg/dL, whereas at the high dose the reductions were more pronounced, reaching 120.7±10.5 mg/dL for Composition 200, 115.8±10.2 mg/dL for Composition 300, 109.9±9.6 mg/dL for Composition 400, and the lowest value of 95.6±8.1 mg/dL for Composition 500. These results demonstrate the glucose-lowering activity of Compositions 200, 300, 400 and 500, with Composition 500 at the high dose producing the strongest effect and reducing fasting glucose to levels approaching those of the physiological control and the glibenclamide group.

TABLE 11

Effects of the experimental compositions on the oral glucose tolerance test in STZ-induced hyperglycemic mice (STZ+)

| | Blood glucose concentration (mg/dL) | |
|---|---|---|
| Experimental group | After 30 minutes | After 120 minute |
| Normal control (STZ−) | 178.5 ± 12.0 | 116.4 ± 9.2 |
| Disease control (STZ+) | 262.8 ± 15.1 | 210.7 ± 16.5 |
| Glibenclamide (5 mg/kg) | 176.6 ± 12.6 | 124.1 ± 9.0 |
| Composition 200, low dose (0.25 g/kg) | 221.4 ± 14.8 | 162.3 ± 12.6 |
| Composition 200, high dose (0.75 g/kg) | 199.2 ± 13.6 | 139.5 ± 11.0 |
| Composition 300, low dose (0.25 g/kg) | 215.8 ± 14.2 | 158.7 ± 12.3 |
| Composition 300, high dose (0.75 g/kg) | 191.6 ± 13.0 | 132.4 ± 10.2 |
| Composition 400, low dose (0.25 g/kg) | 206.2 ± 13.9 | 151.0 ± 11.8 |
| Composition 400, high dose (0.75 g/kg) | 187.4 ± 12.4 | 129.8 ± 10.7 |
| Composition 500, low dose (0.25 g/kg) | 192.8 ± 13.1 | 142.6 ± 11.6 |
| Composition 500, high dose (0.75 g/kg) | 174.3 ± 12.0 | 118.7 ± 9.4 |

Based on the oral glucose tolerance test data in Table 11, all evaluated compositions reduced post-load glucose concentrations compared with the STZ+ disease control group, indicating varying degrees of improvement in glucose tolerance. Specifically, at 30 minutes after glucose loading, the model group exhibited a glucose level of 262.8±15.1 mg/dL, whereas the treated groups showed reductions to approximately 221.4±14.8 and 199.2±13.6 mg/dL for composition 200 at the low and high doses, 215.8±14.2 and 191.6±13.0 mg/dL for composition 300, and 206.2±13.9 and 187.4±12.4 mg/dL for composition 400. For composition 500, the 30-minute post-load glucose concentration reached 192.8±13.1 mg/dL at the low dose and decreased more markedly to 174.3±12.0 mg/dL at the high dose.

A similar trend was observed at 120 minutes, when blood glucose in the model group remained elevated at 210.7±16.5 mg/dL, while the treated groups decreased to 162.3±12.6 and 139.5±11.0 mg/dL for composition 200, 158.7±12.3 and 132.4±10.2 mg/dL for composition 300, and 151.0±11.8 and 129.8±10.7 mg/dL for composition 400. Notably, composition 500 yielded the lowest values at 120 minutes, reaching 142.6±11.6 mg/dL at the low dose and 118.7±9.4 mg/dL at the high dose, approaching the levels of the normal control group and the glibenclamide reference group.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for producing a herbal composition for supporting restoration of digestive system function, comprising the following steps (i) to (vii):

(i) preparing materials comprising:

(a) a *Leucaena leucocephala* extract component having a predetermined first percentage (%) by weight, prepared by mixing a first extract, a second extract and a third extract at a weight ratio of 1:1:2;

wherein the first extract is prepared by performing steps (a1) to (a4):

(a1) preparing material: collecting *Leucaena leucocephala* roots, washing, cutting into pieces, drying to a moisture content of 10%-12%, grinding, and sieving through a 1-2 mm mesh to obtain a first powder;

(a2) extracting the first powder with 60% ethanol at a ratio of 1:30 w/v at a temperature of 50° C.-60° C., in combination with ultrasonic treatment at a frequency of 30 KHz for 30 minutes to obtain a first temporary extract;

(a3) filtering the first temporary extract to remove residues to obtain a filtered first temporary extract; and (a4) concentrating the filtered first temporary extract at a temperature of 65° C.-70° C. until a ratio of the first powder to the first extract reaches (1.5-2):1 w/w to obtain the first extract;

wherein the second extract is prepared by performing steps (a1') to (a4'):

(a1') preparing material: collecting *Leucaena leucocephala* stems, washing, cutting into pieces, drying to a moisture content of 10%-12%, grinding, and sieving through a 1-2 mm mesh to obtain a second powder;

(a2') extracting the second powder with 70% ethanol at a ratio of 1:30 w/v at a temperature of 50° C.-60° C., in combination with ultrasonic treatment at a frequency of 25 kHz for 25 minutes to obtain a second temporary extract;

(a3') filtering the second temporary extract to remove residues to obtain a filtered second temporary extract; and (a4') concentrating the filtered second temporary extract at a temperature of 65° C.-70° C. until a ratio of the second powder to the second extract reaches (1.5-2):1 w/w to obtain the second extract;

wherein the third extract is prepared by performing steps (a1") to (a4"):

(a1") preparing material: collecting *Leucaena leucocephala* seeds, washing, drying to a moisture content of 10%-12%, grinding, and sieving through a 1-2 mm mesh to obtain a third powder;

(a2") extracting the third powder with 70% ethanol at a ratio of 1:30 w/v at a temperature of 50° C.-60° C., in combination with ultrasonic treatment at a frequency of 20 KHz for 20 minutes to obtain a third temporary extract;

(a3") filtering the third temporary extract to remove residues to obtain a filtered third temporary extract; and (a4") concentrating the filtered third temporary extract at a temperature of 65° C.-70° C. until a ratio of the third powder to the third extract reaches (1.5-2):1 w/w to obtain the third extract;

(b) an eleutherin extract component from *Eleutherine bulbosa* having a predetermined second percentage (%) by weight, prepared by performing steps (b1) to (b6):

(b1) preparing material: collecting *Eleutherine bulbosa* tubers, washing, drying to a moisture content of 10%-12%, grinding, and sieving through a 1-2 mm mesh to obtain an *Eleutherine bulbosa* powder;

(b2) extracting the *Eleutherine bulbosa* powder with 96% ethanol at a ratio of 1:25 w/v at a temperature of 50° C.-60° C., in combination with ultrasonic treatment at a frequency of 20 KHz for 20 minutes, and filtering to obtain an *Eleutherine bulbosa* temporary extract;

(b3) concentrating the *Eleutherine bulbosa* temporary extract by rotary evaporation at a temperature of 65° C.-70° C. to obtain an extract residue;

(b4) crystallizing the extract residue at 30° C.-35° C. for 48-72 hours, filtering and washing the crystals with 96% ethanol to obtain a crystalline residue;

(b5) treating the crystalline residue with 5% NaOH solution at 50° C.-60° C. for 10-15 minutes, then recrystallizing the material at 30° C.-35° C. and filtering the crystals from the NaOH solution to obtain alkali-treated crystals; and (b6) dissolving the alkali-treated crystals in 96% ethanol at 30° C.-35° C. to obtain a solution, cooling the solution to 5° C.-10° C. for 2-3 hours, filtering the crystals from ethanol and drying the crystals at 40° C.-50° C. for 90-120 minutes to obtain the eleutherin extract component;

(c) an *Andrographis paniculata* extract component having a predetermined third percentage (%) by weight, prepared by performing steps (c1) to (c4):

(c1) preparing material: collecting *Andrographis paniculata* leaves, washing, drying to a moisture content of 10%-12%, grinding, and sieving through a 1-2 mm mesh to obtain an *Andrographis paniculata* leaf powder;

(c2) extracting the *Andrographis paniculata* leaf powder with 70% ethanol at a ratio of 1:20 w/v at a temperature of 50° C.-60° C., in combination with ultrasonic treatment at a frequency of 25 kHz for 25 minutes, and filtering to remove residues to obtain an *Andrographis paniculata* extract;

(c3) concentrating the *Andrographis paniculata* extract by rotary evaporation at a temperature of 65° C.-70° C. to obtain an *Andrographis paniculata* extract residue; and (c4) mixing the *Andrographis paniculata* extract residue with water at a ratio of 1:1 w/w, then performing liquid-liquid extraction with ethyl acetate (EtOAc) in three repetitions, allowing phase separation and separating the ethyl acetate phase, combining the three ethyl acetate phases, and concentrating at a temperature of 50° C.-60°

C. to remove the solvent, to obtain the *Andrographis paniculata* extract component;

(d) a *Panax vietnamensis* extract component having a predetermined fourth percentage (%) by weight, prepared by mixing a *Panax vietnamensis* root extract with a *Panax vietnamensis* stem and leaf extract at a ratio of 2:1 w/w;

wherein the *Panax vietnamensis* root extract is prepared by performing steps (d1) to (d4):

(d1) preparing material: collecting *Panax vietnamensis* roots of 3-5 years old, washing, cutting into pieces, drying to a moisture content of 10%-12%, grinding, and sieving through a 1-2 mm mesh to obtain a *Panax vietnamensis* root powder;

(d2) mixing the *Panax vietnamensis* root powder with water at a ratio of 1:10 w/w, adding cellulase to achieve an activity of 280-300 U/g in the mixture and adding pectinase to achieve an activity of 220-250 U/g in the mixture, then incubating at a temperature of 45° C.-50° C. with agitation at 120-150 rpm for 1.5-2 hours, followed by ultrasonic-assisted extraction at a frequency of 25 kHz with agitation at 80-100 rpm at 60° C.-65° C. for 25-30 minutes, and centrifuging at 800 rpm for 20 minutes to obtain a solid residue from the root material and a first *Panax vietnamensis* root extract;

(d3) extracting the solid residue from the root material with 60% ethanol at a ratio of 1:20 w/v at a temperature of 50° C.-60° C., in combination with ultrasonic treatment at a frequency of 30 kHz for 30 minutes, and filtering to obtain a second *Panax vietnamensis* root extract; and (d4) combining the first *Panax vietnamensis* root extract and the second *Panax vietnamensis* root extract, concentrating the combined root extract at a temperature of 65° C.-70° C. until a ratio of the *Panax vietnamensis* root powder to the combined root extract reaches (1.5-2):1 w/w to obtain the *Panax vietnamensis* root extract;

wherein the *Panax vietnamensis* stem and leaf extract is prepared by performing steps (d1') to (d4'):

(d1') preparing material: collecting *Panax vietnamensis* stems and leaves, washing, cutting into pieces, drying to a moisture content of 10%-12%, grinding, and sieving through a 1-2 mm mesh to obtain a *Panax vietnamensis* stem and leaf powder;

(d2') mixing the *Panax vietnamensis* stem and leaf powder with water at a ratio of 1:10 w/w, adding cellulase to achieve an activity of 220-250 U/g in the mixture, then incubating at a temperature of 45° C.-50° C. with agitation at 100-120 rpm for 1.5-2 hours, followed by ultrasonic-assisted extraction at a frequency of 20 KHz with agitation at 80-100 rpm at 60° C.-65° C. for 20-25 minutes, and centrifuging at 800 rpm for 20 minutes to obtain a solid residue from the stem and leaf material and a first *Panax vietnamensis* stem and leaf extract;

(d3') extracting the solid residue from the stem and leaf material with 70% ethanol at a ratio of 1:20 w/v at a temperature of 50° C.-60° C., in combination with ultrasonic treatment at a frequency of 20 kHz for 20 minutes, and filtering to obtain a second *Panax vietnamensis* stem and leaf extract; and (d4') combining the first *Panax vietnamensis* stem and leaf extract and the second *Panax vietnamensis* stem and leaf extract, concentrating the combined stem and leaf extract at a temperature of 65° C.-70° C. until a ratio of the *Panax vietnamensis* stem and leaf powder to the combined stem and leaf extract reaches (1.5-2):1 w/w to obtain the *Panax vietnamensis* stem and leaf extract;

(e) a *Pouzolzia zeylanica* extract component having a predetermined fifth percentage (%) by weight, prepared by performing steps (e1) to (e4):

(e1) preparing material: collecting *Pouzolzia zeylanica* stems and leaves, washing, cutting into pieces, drying to a moisture content of 10%-12%, grinding, and sieving through a 1-2 mm mesh to obtain a *Pouzolzia zeylanica* powder;

(e2) mixing the *Pouzolzia zeylanica* powder with water at a weight ratio of 1:10 w/w, adding cellulase to achieve an activity of 280-300 U/g in the mixture, then incubating at a temperature of 45° C.-50° C. with agitation at 100-120 rpm for 1.5-2 hours, followed by ultrasonic-assisted extraction at a frequency of 25 kHz with agitation at 80-100 rpm at 60° C.-65° C. for 20-25 minutes, and centrifuging at 800 rpm for 20 minutes to obtain a solid residue from the material and a first *Pouzolzia zeylanica* extract;

(e3) extracting the solid residue from the material with 70% ethanol at a ratio of 1:20 w/v at a temperature of 50° C.-60° C., in combination with ultrasonic treatment at a frequency of 25 kHz for 30 minutes, and filtering to obtain a second *Pouzolzia zeylanica* extract; and (e4) combining the first *Pouzolzia zeylanica* extract and the second *Pouzolzia zeylanica* extract, concentrating the combined extract at a temperature of 65° C.-70° C. until a ratio of the *Pouzolzia zeylanica* powder to the combined extract reaches (1.5-2):1 w/w to obtain the *Pouzolzia zeylanica* extract component;

(f) a first herbal mixture extract component having a predetermined sixth percentage (%) by weight, prepared by performing steps (f1) to (f4):

(f1) preparing a first herbal mixture powder by mixing six herbals at a weight ratio of 2 parts of *Curcuma zedoaria* root, 2 parts of *Curcuma longa* root, 2 parts of *Zingiber officinale* root, 2 parts of *Alpinia galanga* root, 1 part of *Platycodon grandiflorus* root and 1 part of *Citrus aurantium* fruit, each herbal having a moisture content of 10%-12%, and grinding and sieving the blended materials through a 1-2 mm mesh to obtain a first herbal mixture powder;

(f2) mixing the first herbal mixture powder with water at a ratio of 1:(15-20) w/w, adding cellulase to achieve an activity of 650-700 U/g in the mixture and adding pectinase to achieve an activity of 450-500 U/g in the mixture, then incubating at a temperature of 40° C.-45° C. with agitation at 100-150 rpm for 2-3 hours, followed by ultrasonic-assisted extraction at a frequency of 30 KHz with agitation at 80-100 rpm at 65° C.-70° C. for 30 minutes, and centrifuging at 800 rpm for 20 minutes to obtain a solid residue from the first herbal mixture and a first extract of the first herbal mixture;

(f3) extracting the solid residue from the first herbal mixture with 70% ethanol at a ratio of 1:(10-15) w/v at a temperature of 55° C.-60° C., in combination with ultrasonic treatment at a frequency of 25 kHz with agitation at 80-100 rpm for 20 minutes, followed by centrifuging at 800 rpm for 20 minutes and filtering to obtain a second extract of the first herbal mixture; and (f4) combining the first extract of the first herbal mixture and the second extract of the first herbal mixture, concentrating the combined first herbal mixture extract at a temperature of 65° C.-70° C. until a ratio of the first herbal mixture powder to the combined first herbal mixture extract reaches (1.5-2):1 w/w to obtain the first herbal mixture extract component;

(g) a second herbal mixture extract component having a predetermined seventh percentage (%) by weight, prepared by performing steps (g1) to (g4):

(g1) preparing a second herbal mixture by mixing five herbals at a weight ratio of 3 parts of *Plumbago zeylanica* stem, 3 parts of *Cleistocalyx operculatus* leaf, 2 parts of *Ampelopsis cantoniensis* leaf, 1 part of whole plant of *Lycopodiella cernua*, and 1 part of *Ficus carica* fruit, each herbal material having a moisture content of 10%-12%, and grinding and sieving the blended materials through a 1-2 mm mesh to obtain a second herbal mixture powder;

(g2) mixing the second herbal mixture powder with water at a weight ratio of 1:(20-25) w/w, adding cellulase to achieve an activity of 550-600 U/g in the mixture and adding pectinase to achieve an activity of 350-400 U/g in the mixture, incubating at a temperature of 40° C.-45° C. with agitation at 100-150 rpm for 2-3 hours, followed by ultrasonic-assisted extraction at a frequency of 30 kHz with agitation at 80-100 rpm at 65° C.-70° C. for 30 minutes, and centrifuging at 800 rpm for 20 minutes to obtain a solid residue from the second herbal mixture and a first extract of the second herbal mixture;

(g3) extracting the solid residue from the second herbal mixture with 70% ethanol at a ratio of 1:(10-15) w/v at a temperature of 55° C.-60° C., in combination with ultrasonic treatment at a frequency of 20 KHz with agitation at 80-100 rpm for 20 minutes, followed by centrifuging at 800 rpm for 20 minutes and removing the solid residue to obtain a second extract of the second herbal mixture; and (g4) combining the first extract of the second herbal mixture and the second extract of the second herbal mixture, concentrating the combined second herbal mixture extract at a temperature of 65° C.-70° C. until a ratio of the second herbal mixture powder to the combined second herbal mixture extract reaches (1.5-2):1 w/w to obtain the second herbal mixture extract component;

(h) a sugar component having a predetermined eighth percentage (%) by weight; wherein the sugar component is selected from the group consisting of glucose, fructose, galactose, lactose, maltose, sucrose, and combinations thereof;

(i) a salt component having a predetermined ninth percentage (%) by weight;

wherein the salt component is selected from the group consisting of sea salt, himalayan pink salt, kosher salt, and combinations thereof;

(j) a honey component having a predetermined tenth percentage (%) by weight;

(k) a royal jelly component having a predetermined eleventh percentage (%) by weight;

(l) a vegetable oil component having a predetermined twelfth percentage (%) by weight; wherein the vegetable oil component is selected from the group consisting of rice bran oil, sunflower oil, olive oil, and combinations thereof; and (m) a plant powder component having a predetermined thirteenth percentage (%) by weight; wherein the plant powder component is selected from the group consisting of rice flour, wheat flour, cereal flour, and combinations thereof; wherein the cereal flour is obtained by mixing five legume seed powders at a weight ratio of 1 part of *Vigna unguiculata* seed powder, 1 part of *Glycine max* seed powder, 1 part of *Vigna radiata* seed powder, 1 part of *Vigna angularis* seed powder, and 1 part of *Phaseolus vulgaris* seed powder;

(ii) heating the honey component at 65° C.-70° C., adding the royal jelly component, the sugar component and the salt component, then stirring at 500-600 rpm for 45 minutes to obtain a base mixture;

(iii) mixing the plant powder component with the base mixture at step (ii) and stirring at 400-500 rpm for 30 minutes to obtain a first temporary mixture;

(iv) mixing the components (a) to (g) in order with the first temporary mixture at step (iii) to obtain a second temporary mixture, ensuring homogeneous mixing after each addition;

(v) mixing the vegetable oil component with the second temporary mixture at step (iv) and stirring at 400-500 rpm for 30 minutes to obtain a third temporary mixture;

(vi) creating a fermented mixture by performing steps (i') to (iii'):

(i') preparing ingredients comprising a substrate mixture and a fermentation microbial mixture; wherein the substrate mixture is obtained by sterilizing the third temporary mixture at step (v) by autoclaving at 121° C. for 15 minutes; wherein the fermentation microbial mixture is obtained by mixing a first microbial biomass, a second microbial biomass, a third microbial biomass and a fourth microbial biomass at a weight ratio of 1:1:1:1; wherein the first microbial biomass is obtained by culturing *Lactobacillus plantarum* ATCC 14917 on a propagation medium for 24 hours at 37° C., then centrifuging at 4° C. at 6000 rpm for 10 minutes, removing the supernatant and collecting the microbial pellet to obtain the first microbial biomass; the second microbial biomass is obtained by culturing *Lactobacillus fermentum* ATCC 23271 on a propagation medium for 24 hours at 37° C., then centrifuging at 4° C. at 6000 rpm for 10 minutes, removing the supernatant and collecting the microbial pellet to obtain the second microbial biomass; the third microbial biomass is obtained by culturing *Lactobacillus rhamnosus* ATCC 53103 on a propagation medium for 24 hours at 37° C., then centrifuging at 4° C. at 6000 rpm for 10 minutes, removing the supernatant and collecting the microbial pellet to obtain the third microbial biomass; and the fourth microbial biomass is obtained by culturing *Lactobacillus paracasei* ATCC 25598 on a propagation medium for 24 hours at 37° C., then centrifuging at 4° C. at 6000 rpm for 10 minutes, removing the supernatant and collecting the microbial pellet to obtain the fourth microbial biomass;

wherein the propagation medium comprises glucose 20 g/L, peptone 10 g/L, yeast extract 5 g/L, $CaCO_3$ 5 g/L, $K_2HPO_4$ 2 g/L, $MgSO_4$ 0.6 g/L, and $MnSO_4$ 0.3 g/L;

(ii') mixing the fermentation microbial mixture with the substrate mixture at a ratio of (1-2):100 w/w, and mixing until homogeneous to obtain a fermentation substrate mixture; and (iii') fermenting the fermentation substrate mixture at 30° C.-35° C. for 40-48 hours to obtain the fermented mixture;

wherein the total viable cell density in the fermented mixture is $1×10^7$ to $1×10^9$ CFU/g; and (vii) packaging the fermented mixture at step (vi) to obtain the herbal composition for supporting restoration of digestive system function.

2. The method of claim 1, wherein the predetermined first percentage (%) by weight is 6%-8%, the predetermined second percentage (%) by weight is 4%-6%, the predetermined third percentage (%) by weight is 3%-5%, the predetermined fourth percentage (%) by weight is 6%-8%, the predetermined fifth percentage (%) by weight is 4%-6%, the predetermined sixth percentage (%) by weight is 18%-20%, the predetermined seventh percentage (%) by weight is 12%-14%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

3. The method of claim 1, wherein the predetermined first percentage (%) by weight is 4%-6%, the predetermined second percentage (%) by weight is 4%-6%, the predetermined third percentage (%) by weight is 8%-10%, the predetermined fourth percentage (%) by weight is 6%-8%, the predetermined fifth percentage (%) by weight is 2%-4%, the predetermined sixth percentage (%) by weight is 18%-20%, the predetermined seventh percentage (%) by weight is 10%-12%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

4. The method of claim 1, wherein the predetermined first percentage (%) by weight is 6%-8%, the predetermined second percentage (%) by weight is 4%-5%, the predetermined third percentage (%) by weight is 3%-4%, the predetermined fourth percentage (%) by weight is 6%-8%, the predetermined fifth percentage (%) by weight is 6%-8%, the predetermined sixth percentage (%) by weight is 6%-8%, the predetermined seventh percentage (%) by weight is 12%-

14%, the predetermined eighth percentage (%) by weight is 3%-4%, the predetermined ninth percentage (%) by weight is 0.5%-1.5%, the predetermined tenth percentage (%) by weight is 10%-12%, the predetermined eleventh percentage (%) by weight is 10%-12%, the predetermined twelfth percentage (%) by weight is 2%-3%, and the thirteenth percentage (%) by weight is the remainder to make up 100% by weight.

5. The method of claim 1, wherein the predetermined first percentage (%) by weight is 4%-6%, the predetermined second percentage (%) by weight is 5%-6%, the predetermined third percentage (%) by weight is 5%-7%, the predetermined fourth percentage (%) by weight is 14%-16%, the predetermined fifth percentage (%) by weight is 4%-6%, the predetermined sixth percentage (%) by weight is 16%-18%, the predetermined seventh percentage (%) by weight is 8%-10%, the predetermined eighth percentage (%) by weight is 2%-3%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

6. The method of claim 1, wherein the sugar component is sucrose.

7. The method of claim 1, wherein the salt component is obtained by mixing sea salt and himalayan pink salt at a weight ratio of 1:1.

8. The method of claim 1, wherein the vegetable oil component is obtained by mixing rice bran oil, sunflower oil, and olive oil at a weight ratio of 2:1:1.

9. The method of claim 1, wherein the plant powder component is obtained by mixing rice flour, wheat flour, and cereal flour at a weight ratio of 1:1:1.

10. A herbal composition for supporting restoration of digestive system function comprising: a *Leucaena leucocephala* extract component having a predetermined first percentage (%) by weight, an eleutherin extract component from *Eleutherine bulbosa* having a predetermined second percentage (%) by weight, an *Andrographis paniculata* extract component having a predetermined third percentage (%) by weight, a *Panax vietnamensis* extract component having a predetermined fourth percentage (%) by weight, a *Pouzolzia zeylanica* extract component having a predetermined fifth percentage (%) by weight, a first herbal mixture extract component having a predetermined sixth percentage (%) by weight, a second herbal mixture extract component having a predetermined seventh percentage (%) by weight, a sugar component having a predetermined eighth percentage (%) by weight, a salt component having a predetermined ninth percentage (%) by weight, a honey component having a predetermined tenth percentage (%) by weight, a royal jelly component having a predetermined eleventh percentage (%) by weight, a vegetable oil component having a predetermined twelfth percentage (%) by weight, and a plant powder component having a predetermined thirteenth percentage (%) by weight; wherein said herbal composition is produced by a process comprising the following steps:

(i) preparing materials comprising:

(a) a *Leucaena leucocephala* extract component having a predetermined first percentage (%) by weight, prepared by mixing a first extract, a second extract and a third extract at a weight ratio of 1:1:2;

wherein the first extract is prepared by performing steps (a1) to (a4):

(a1) preparing material: collecting *Leucaena leucocephala* roots, washing, cutting into pieces, drying to a moisture content of 10%-12%, grinding, and sieving through a 1-2 mm mesh to obtain a first powder;

(a2) extracting the first powder with 60% ethanol at a ratio of 1:30 w/v at a temperature of 50° C.-60° C., in combination with ultrasonic treatment at a frequency of 30 kHz for 30 minutes to obtain a first temporary extract;

(a3) filtering the first temporary extract to remove residues to obtain a filtered first temporary extract; and (a4) concentrating the filtered first temporary extract at a temperature of 65° C.-70° C. until a weight ratio of the first powder to the first extract reaches (1.5-2):1 to obtain the first extract;

wherein the second extract is prepared by performing steps (a1') to (a4'):

(a1') preparing material: collecting *Leucaena leucocephala* stems, washing, cutting into pieces, drying to a moisture content of 10%-12%, grinding, and sieving through a 1-2 mm mesh to obtain a second powder;

(a2') extracting the second powder with 70% ethanol at a ratio of 1:30 w/v at a temperature of 50° C.-60° C., in combination with ultrasonic treatment at a frequency of 25 kHz for 25 minutes to obtain a second temporary extract;

(a3') filtering the second temporary extract to remove residues to obtain a filtered second temporary extract; and (a4') concentrating the filtered second temporary extract at a temperature of 65° C.-70° C. until a ratio of the second powder to the second extract reaches (1.5-2):1 w/w to obtain the second extract;

wherein the third extract is prepared by performing steps (a1") to (a4"):

(a1") preparing material: collecting *Leucaena leucocephala* seeds, washing, drying to a moisture content of 10%-12%, grinding, and sieving through a 1-2 mm mesh to obtain a third powder;

(a2") extracting the third powder with 70% ethanol at a ratio of 1:30 w/v at a temperature of 50° C.-60° C., in combination with ultrasonic treatment at a frequency of 20 KHz for 20 minutes to obtain a third temporary extract;

(a3") filtering the third temporary extract to remove residues to obtain a filtered third temporary extract; and (a4") concentrating the filtered third temporary extract at a temperature of 65° C.-70° C. until a ratio of the third powder to the third extract reaches (1.5-2):1 w/w to obtain the third extract;

(b) an eleutherin extract component from *Eleutherine bulbosa* having a predetermined second percentage (%) by weight, prepared by performing steps (b1) to (b6):

(b1) preparing material: collecting *Eleutherine bulbosa* tubers, washing, drying to a moisture content of 10%-12%, grinding, and sieving through a 1-2 mm mesh to obtain an *Eleutherine bulbosa* powder;

(b2) extracting the *Eleutherine bulbosa* powder with 96% ethanol at a ratio of 1:25 w/v at a temperature of 50° C.-60° C., in combination with ultrasonic treatment at a frequency of 20 kHz for 20 minutes, and filtering to obtain an *Eleutherine bulbosa* temporary extract;

(b3) concentrating the *Eleutherine bulbosa* temporary extract by rotary evaporation at a temperature of 65° C.-70° C. to obtain an extract residue;

(b4) crystallizing the extract residue at 30° C.-35° C. for 48-72 hours, filtering and washing the crystals with 96% ethanol to obtain a crystalline residue;

(b5) treating the crystalline residue with 5% NaOH solution at 50° C.-60° C. for 10-15 minutes, then recrystallizing the material at 30° C.-35° C. and filtering the crystals from the NaOH solution to obtain alkali-treated crystals; and (b6) dissolving the alkali-treated crystals in 96% ethanol at 30° C.-35° C. to obtain a solution, cooling the solution to 5° C.-10° C. for 2-3 hours, filtering the crystals from ethanol and drying the crystals at 40° C.-50° C. for 90-120 minutes to obtain the eleutherin extract component;

(c) an *Andrographis paniculata* extract component having a predetermined third percentage (%) by weight, prepared by performing steps (c1) to (c4):

(c1) preparing material: collecting *Andrographis paniculata* leaves, washing, drying to a moisture content of 10%-12%, grinding, and sieving through a 1-2 mm mesh to obtain an *Andrographis paniculata* leaf powder;

(c2) extracting the *Andrographis paniculata* leaf powder with 70% ethanol at a ratio of 1:20 w/v at a temperature of 50° C.-60° C., in combination with ultrasonic treatment at a frequency of 25 kHz for 25 minutes, and filtering to remove residues to obtain an *Andrographis paniculata* extract;

(c3) concentrating the *Andrographis paniculata* extract by rotary evaporation at a temperature of 65° C.-70° C. to obtain an *Andrographis paniculata* extract residue; and (c4) mixing the *Andrographis paniculata* extract residue with water at a ratio of 1:1 w/w, then performing liquid-liquid extraction with ethyl acetate (EtOAc) in three repetitions, allowing phase separation and separating the ethyl acetate phase, combining the three ethyl acetate phases, and concentrating at a temperature of 50° C.-60° C. to remove the solvent, to obtain the *Andrographis paniculata* extract component;

(d) a *Panax vietnamensis* extract component having a predetermined fourth percentage (%) by weight, prepared by mixing a *Panax vietnamensis* root extract with a *Panax vietnamensis* stem and leaf extract at a ratio of 2:1 w/w;

wherein the *Panax vietnamensis* root extract is prepared by performing steps (d1) to (d4):

(d1) preparing material: collecting *Panax vietnamensis* roots of 3-5 years old, washing, cutting into pieces, drying to a moisture content of 10%-12%, grinding, and sieving through a 1-2 mm mesh to obtain a *Panax vietnamensis* root powder;

(d2) mixing the *Panax vietnamensis* root powder with water at a ratio of 1:10 w/w, adding cellulase to achieve an activity of 280-300 U/g in the mixture and adding pectinase to achieve an activity of 220-250 U/g in the mixture, then incubating at a temperature of 45° C.-50° C. with agitation at 120-150 rpm for 1.5-2 hours, followed by ultrasonic-assisted extraction at a frequency of 25 kHz with agitation at 80-100 rpm at 60° C.-65° C. for 25-30 minutes, and centrifuging at 800 rpm for 20 minutes to obtain a solid residue from the root material and a first *Panax vietnamensis* root extract;

(d3) extracting the solid residue from the root material with 60% ethanol at a ratio of 1:20 w/v at a temperature of 50° C.-60° C., in combination with ultrasonic treatment at a frequency of 30 KHz for 30 minutes, and filtering to obtain a second *Panax vietnamensis* root extract; and (d4) combining the first *Panax vietnamensis* root extract and the second *Panax vietnamensis* root extract, concentrating the combined root extract at a temperature of 65° C.-70° C. until a ratio of the *Panax vietnamensis* root powder to the combined root extract reaches (1.5-2):1 w/w to obtain the *Panax vietnamensis* root extract;

wherein the *Panax vietnamensis* stem and leaf extract is prepared by performing steps (d1') to (d4'):

(d1') preparing material: collecting *Panax vietnamensis* stems and leaves, washing, cutting into pieces, drying to a moisture content of 10%-12%, grinding, and sieving through a 1-2 mm mesh to obtain a *Panax vietnamensis* stem and leaf powder;

(d2') mixing the *Panax vietnamensis* stem and leaf powder with water at a ratio of 1:10 w/w, adding cellulase to achieve an activity of 220-250 U/g in the mixture, then incubating at a temperature of 45° C.-50° C. with agitation at 100-120 rpm for 1.5-2 hours, followed by ultrasonic-assisted extraction at a frequency of 20 KHz with agitation at 80-100 rpm at 60° C.-65° C. for 20-25 minutes, and centrifuging at 800 rpm for 20 minutes to obtain a solid residue from the stem and leaf material and a first *Panax vietnamensis* stem and leaf extract;

(d3') extracting the solid residue from the stem and leaf material with 70% ethanol at a ratio of 1:20 w/v at a temperature of 50° C.-60° C., in combination with ultrasonic treatment at a frequency of 20 kHz for 20 minutes, and filtering to obtain a second *Panax vietnamensis* stem and leaf extract; and (d4') combining the first *Panax vietnamensis* stem and leaf extract and the second *Panax vietnamensis* stem and leaf extract, concentrating the combined stem and leaf extract at a temperature of 65° C.-70° C. until a ratio of the *Panax vietnamensis* stem and leaf powder to the combined stem and leaf extract reaches (1.5-2):1 w/w to obtain the *Panax vietnamensis* stem and leaf extract;

(e) a *Pouzolzia zeylanica* extract component having a predetermined fifth percentage (%) by weight, prepared by performing steps (e1) to (e4):

(e1) preparing material: collecting *Pouzolzia zeylanica* stems and leaves, washing, cutting into pieces, drying to a moisture content of 10%-12%, grinding, and sieving through a 1-2 mm mesh to obtain a *Pouzolzia zeylanica* powder;

(e2) mixing the *Pouzolzia zeylanica* powder with water at a weight ratio of 1:10 w/w, adding cellulase to achieve an activity of 280-300 U/g in the mixture, then incubating at a temperature of 45° C.-50° C. with agitation at 100-120 rpm for 1.5-2 hours, followed by ultrasonic-assisted extraction at a frequency of 25 KHz with agitation at 80-100 rpm at 60° C.-65° C. for 20-25 minutes, and centrifuging at 800 rpm for 20 minutes to obtain a solid residue from the material and a first *Pouzolzia zeylanica* extract;

(e3) extracting the solid residue from the material with 70% ethanol at a ratio of 1:20 w/v at a temperature of 50° C.-60° C., in combination with ultrasonic treatment at a frequency of 25 kHz for 30 minutes, and filtering to obtain a second *Pouzolzia zeylanica* extract; and (e4) combining the first *Pouzolzia zeylanica* extract and the second *Pouzolzia zeylanica* extract, concentrating the combined extract at a temperature of 65° C.-70° C. until a ratio of the *Pouzolzia zeylanica* powder to the combined extract reaches (1.5-2):1 w/w to obtain the *Pouzolzia zeylanica* extract component;

(f) a first herbal mixture extract component having a predetermined sixth percentage (%) by weight, prepared by performing steps (f1) to (f4):

(f1) preparing a first herbal mixture powder by mixing six herbals at a weight ratio of 2 parts of *Curcuma zedoaria* root, 2 parts of *Curcuma longa* root, 2 parts of *Zingiber officinale* root, 2 parts of *Alpinia galanga* root, 1 part of *Platycodon grandiflorus* root and 1 part of *Citrus aurantium* fruit, each herbal having a moisture content of 10%-12%, and grinding and sieving the blended materials through a 1-2 mm mesh to obtain a first herbal mixture powder;

(f2) mixing the first herbal mixture powder with water at a ratio of 1:(15-20) w/w, adding cellulase to achieve an activity of 650-700 U/g in the mixture and adding pectinase to achieve an activity of 450-500 U/g in the mixture, then incubating at a temperature of 40° C.-45° C. with agitation at 100-150 rpm for 2-3 hours, followed by ultrasonic-assisted extraction at a frequency of 30 kHz with agitation at 80-100 rpm at 65° C.-70° C. for 30 minutes, and centrifuging at 800 rpm for 20 minutes to obtain a solid residue from the first herbal mixture and a first extract of the first herbal mixture;

(f3) extracting the solid residue from the first herbal mixture with 70% ethanol at a ratio of 1:(10-15) w/v at a temperature of 55° C.-60° C., in combination with ultrasonic treatment at a frequency of 25 kHz with agitation at 80-100 rpm for 20 minutes, followed by centrifuging at 800 rpm for 20 minutes and filtering to obtain a second extract of the first herbal mixture; and (f4) combining the first extract of the first herbal mixture and the second extract of the first herbal mixture, concentrating the combined first herbal mixture extract at a temperature of 65° C.-70° C. until a ratio of the first herbal mixture powder to the combined first herbal mixture extract reaches (1.5-2):1 w/w to obtain the first herbal mixture extract component;

(g) a second herbal mixture extract component having a predetermined seventh percentage (%) by weight, prepared by performing steps (g1) to (g4):

(g1) preparing a second herbal mixture by mixing five herbals at a weight ratio of 3 parts of *Plumbago zeylanica* stem, 3 parts of *Cleistocalyx operculatus* leaf, 2 parts of *Ampelopsis cantoniensis* leaf, 1 part of whole plant of *Lycopodiella cernua*, and 1 part of *Ficus carica* fruit, each herbal material having a moisture content of 10%-12%, and grinding and sieving the blended materials through a 1-2 mm mesh to obtain a second herbal mixture powder;

(g2) mixing the second herbal mixture powder with water at a weight ratio of 1:(20-25) w/w, adding cellulase to achieve an activity of 550-600 U/g in the mixture and adding pectinase to achieve an activity of 350-400 U/g in the mixture, incubating at a temperature of 40° C.-45° C. with agitation at 100-150 rpm for 2-3 hours, followed by ultrasonic-assisted extraction at a frequency of 30 kHz with agitation at 80-100 rpm at 65° C.-70° C. for 30 minutes, and centrifuging at 800 rpm for 20 minutes to obtain a solid residue from the second herbal mixture and a first extract of the second herbal mixture;

(g3) extracting the solid residue from the second herbal mixture with 70% ethanol at a ratio of 1:(10-15) w/v at a temperature of 55° C.-60° C., in combination with ultrasonic treatment at a frequency of 20 kHz with agitation at 80-100 rpm for 20 minutes, followed by centrifuging at 800 rpm for 20 minutes and removing the solid residue to obtain a second extract of the second herbal mixture; and (g4) combining the first extract of the second herbal mixture and the second extract of the second herbal mixture, concentrating the combined second herbal mixture extract at a temperature of 65° C.-70° C. until a ratio of the second herbal mixture powder to the combined second herbal mixture extract reaches (1.5-2):1 w/w to obtain the second herbal mixture extract component;

(h) a sugar component having a predetermined eighth percentage (%) by weight;

wherein the sugar component is selected from the group consisting of glucose, fructose, galactose, lactose, maltose, sucrose, and combinations thereof;

(i) a salt component having a predetermined ninth percentage (%) by weight;

wherein the salt component is selected from the group consisting of sea salt, himalayan pink salt, kosher salt, and combinations thereof;

(j) a honey component having a predetermined tenth percentage (%) by weight;

(k) a royal jelly component having a predetermined eleventh percentage (%) by weight;

(l) a vegetable oil component having a predetermined twelfth percentage (%) by weight;

wherein the vegetable oil component is selected from the group consisting of rice bran oil, sunflower oil, olive oil, and combinations thereof; and (m) a plant powder component having a predetermined thirteenth percentage (%) by weight;

wherein the plant powder component is selected from the group consisting of rice flour, wheat flour, cereal flour, and combinations thereof;

wherein the cereal flour is obtained by mixing five legume seed powders at a weight ratio of 1 part of *Vigna unguiculata* seed powder, 1 part of *Glycine max* seed powder, 1 part of *Vigna*

*radiata* seed powder, 1 part of *Vigna angularis* seed powder, and 1 part of *Phaseolus vulgaris* seed powder;

(ii) heating the honey component at 65° C.-70° C., adding the royal jelly component, the sugar component and the salt component, then stirring at 500-600 rpm for 45 minutes to obtain a base mixture;

(iii) mixing the plant powder component with the base mixture at step (ii) and stirring at 400-500 rpm for 30 minutes to obtain a first temporary mixture;

(iv) mixing the components (a) to (g) in order with the first temporary mixture at step (iii) to obtain a second temporary mixture, ensuring homogeneous mixing after each addition; and (v) mixing the vegetable oil component with the second temporary mixture at step (iv) and stirring at 400-500 rpm for 30 minutes to obtain a third temporary mixture;

(vi) creating a fermented mixture by performing steps (i') to (iii'):

(i') preparing ingredients comprising a substrate mixture and a fermentation microbial mixture;

wherein the substrate mixture is obtained by sterilizing the third temporary mixture at step (v) by autoclaving at 121° C. for 15 minutes;

wherein the fermentation microbial mixture is obtained by mixing a first microbial biomass, a second microbial biomass, a third microbial biomass and a fourth microbial biomass at a weight ratio of 1:1:1:1; wherein the first microbial biomass is obtained by culturing *Lactobacillus plantarum* ATCC 14917 on a propagation medium for 24 hours at 37° C., then centrifuging at 4° C. at 6000 rpm for 10 minutes, removing the supernatant and collecting the microbial pellet to obtain the first microbial biomass;

the second microbial biomass is obtained by culturing *Lactobacillus fermentum* ATCC 23271 on a propagation medium for 24 hours at 37° C., then centrifuging at 4° C. at 6000 rpm for 10 minutes, removing the supernatant and collecting the microbial pellet to obtain the second microbial biomass;

the third microbial biomass is obtained by culturing *Lactobacillus rhamnosus* ATCC 53103 on a propagation medium for 24 hours at 37° C., then centrifuging at 4° C. at 6000 rpm for 10 minutes, removing the supernatant and collecting the microbial pellet to obtain the third microbial biomass; and the fourth microbial biomass is obtained by culturing *Lactobacillus paracasei* ATCC 25598 on a propagation medium for 24 hours at 37° C., then centrifuging at 4° C. at 6000 rpm for 10 minutes, removing the supernatant and collecting the microbial pellet to obtain the fourth microbial biomass;

wherein the propagation medium comprises glucose 20 g/L, peptone 10 g/L, yeast extract 5 g/L, $CaCO_3$ 5 g/L, $K_2HPO_4$ 2 g/L, $MgSO_4$ 0.6 g/L, and $MnSO_4$ 0.3 g/L;

(ii') mixing the fermentation microbial mixture with the substrate mixture at a ratio of (1-2):100 w/w, and mixing until homogeneous to obtain a fermentation substrate mixture; and (iii') fermenting the fermentation substrate mixture at 30° C.-35° C. for 40-48 hours to obtain the fermented mixture;

wherein the total viable cell density in the fermented mixture is $1 \times 10^7$ to $1 \times 10^9$ CFU/g; and (vii) packaging the fermented mixture at step (vi) to obtain the herbal composition for supporting restoration of digestive system function.

11. The composition of claim 10, wherein the predetermined first percentage (%) by weight is 6%-8%, the predetermined second percentage (%) by weight is 4%-6%, the predetermined third percentage (%) by weight is 3%-5%, the predetermined fourth percentage (%) by weight is 6%-8%, the predetermined fifth percentage (%) by weight is 4%-6%, the predetermined sixth percentage (%) by weight is 18%-20%, the predetermined seventh percentage (%) by weight is 12%-14%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

12. The composition of claim 10, wherein the predetermined first percentage (%) by weight is 4%-6%, the predetermined second percentage (%) by weight is 4%-6%, the predetermined third percentage (%) by weight is 8%-10%, the predetermined fourth percentage (%) by weight is 6%-8%, the predetermined fifth percentage (%) by weight is 2%-4%, the predetermined sixth percentage (%) by weight is 18%-20%, the predetermined seventh percentage (%) by weight is 10%-12%, the predetermined eighth percentage (%) by weight is 4%-6%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

13. The composition of claim 10, wherein the predetermined first percentage (%) by weight is 6%-8%, the predetermined second percentage (%) by weight is 4%-5%, the predetermined third percentage (%) by weight is 3%-4%, the predetermined fourth percentage (%) by weight is 6%-8%, the predetermined fifth percentage (%) by weight is 6%-8%, the predetermined sixth percentage (%) by weight is 6%-8%, the predetermined seventh percentage (%) by weight is 12%-14%, the predetermined eighth percentage (%) by weight is 3%-4%, the predetermined ninth percentage (%) by weight is 0.5%-1.5%, the predetermined tenth percentage (%) by weight is 10%-12%, the predetermined eleventh percentage (%) by weight is 10%-12%, the predetermined twelfth percentage (%) by weight is 2%-3%, and the thirteenth percentage (%) by weight is the remainder to make up 100% by weight.

14. The composition of claim 10, wherein the predetermined first percentage (%) by weight is 4%-6%, the predetermined second percentage (%) by weight is 5%-6%, the predetermined third percentage (%) by weight is 5%-7%, the predetermined fourth percentage (%) by weight is 14%-16%, the predetermined fifth percentage (%) by weight is 4%-6%, the predetermined sixth percentage (%) by weight is 16%-18%, the predetermined seventh percentage (%) by weight is 8%-10%, the predetermined eighth percentage (%) by weight is 2%-3%, the predetermined ninth percentage (%) by weight is 0.5%-1.5%, the predetermined tenth percentage (%) by weight is 8%-10%, the predetermined eleventh percentage (%) by weight is 8%-10%, the predetermined twelfth percentage (%) by weight is 2%-3%, and the thirteenth percentage (%) by weight is the remainder to make up 100% by weight.

15. The composition of claim 10, wherein the sugar component is sucrose.

16. The composition of claim 10, wherein the salt component is obtained by mixing sea salt and himalayan pink salt at a weight ratio of 1:1.

17. The composition of claim 10, wherein the vegetable oil component is obtained by mixing rice bran oil, sunflower oil, and olive oil at a weight ratio of 2:1:1.

18. The composition of claim 10, wherein the plant powder component is obtained by mixing rice flour, wheat flour, and cereal flour at a weight ratio of 1:1:1.

\* \* \* \* \*